(12) United States Patent
Wolf et al.

(10) Patent No.: US 7,829,331 B2
(45) Date of Patent: Nov. 9, 2010

(54) USE OF UREA-ADJUVATED POLYPEPTIDES FOR DIAGNOSIS, PROPHYLAXIS AND TREATMENT

(75) Inventors: Hans Wolf, Josef Jägerhuberstrasse 9, 82319 Starnberg (DE); Ludwig Deml, Regenstauf (DE); Kerstin Püllmann, Regensburg (DE)

(73) Assignee: Hans Wolf, Starnberg (DE)

( * ) Notice: Subject to any disclaimer, the term of this patent is extended or adjusted under 35 U.S.C. 154(b) by 0 days.

(21) Appl. No.: 10/508,642

(22) PCT Filed: Mar. 19, 2003

(86) PCT No.: PCT/DE03/00917

§ 371 (c)(1),
(2), (4) Date: Jun. 16, 2005

(87) PCT Pub. No.: WO03/080792

PCT Pub. Date: Oct. 2, 2003

(65) Prior Publication Data

US 2006/0057108 A1 Mar. 16, 2006

(30) Foreign Application Priority Data

Mar. 22, 2002 (DE) .................. 102 12 867

(51) Int. Cl.
*C12N 5/071* (2010.01)
*C12N 5/00* (2010.01)
*C12N 5/02* (2010.01)

(52) U.S. Cl. ................... 435/372.3; 435/373
(58) Field of Classification Search ............. None
See application file for complete search history.

(56) References Cited

FOREIGN PATENT DOCUMENTS

GB 1 128 005 A 9/1968

OTHER PUBLICATIONS

Prabhakar et al., 1997, Urea inhibits inducible nitric oxide synthase in macrophage cell line. Am. J. Phys. vol. 273: 1882-1888.*
"Liquor" Stedmans medical dictionary 27th edition, 2000. Doucett et al., 2005, J. Immunol. Methods, vol. 303: 40-52.*
Pala et al., 2000, J. Immunol. Methods, vol. 243: 107-24.*
Broff et al., 1981, Eur. J. Immunol. vol. 11: 365-71.*
Van Kaer et al., 2005, Curr Biol. vol. 15:R429-31.*
Sone et al., 1998, J. Immunol. vol. 161: 448-457.*
Kessler et al., 1999, Clinical Chemistry, vol. 45: 1523-1529.*
Invitrogen Technical Resources-Medial Formulations, 2008, pp. 1-3.*
Schenk et al., 1995, J. Allergy Clin. Immunol. vol. 96: 986-996.*
Sheil et al., 1992, J. Exp. Med. vol. 175: 545-552.*
Kerblat et al., 2000, immunology, vol. 100: 178-184.*
Nagahara et al., 1998, Nat. Med. vol. 4: 1449-1452.*
Bauer et al., "Induction of MHC class-I and -II restricted epitope presentation by urea-treated BZLF1 protein: a novel technology for the detection of protein-specific cytotoxic t-cells," *Proceedings of the EBV2002 Conference*, p. 34, 2002.
Elliot et al., "Dominant cytotoxic T Lymphocyte response to the immediate-early *trans*-activator protein, BZLF1, in persistent type A or B Epstein-Barr virus infection," *Journal of Infectious Diseases*, 176:1068-1072, 1997.
Jenne et al., "Viral vectors for dendritic cell-based immunotherapy," *Trends Immunol.*, 22(2):102-107, 2001.
Mi et al., "Characterization of a class of cationic peptides able to facilitate efficient protein transduction in vitro and in vivo," *Mol. Ther.* 2(4):339-347, 2000.
O'Hagan et al., "Recent developments in adjuvants for vaccines against infectious diseases," *Biomol Engin.*, 18:69-85, 2001.
Schirmbeck et al., "Injection of detergent-denatured ovalbumin primes murine class I-restricted cytotoxic T cells in vivo," *Eur. J. Immunol.*, 24:2068, 1994.
Schirmbeck et al., "Priming of class I-restricted cytotoxic T lymphocytes by vaccination with recombinant protein antigens," *Vaccine*, 13:857-865, 1995.
Schwarze et al., "Protein transduction: unrestricted delivery into all cells?" *Trends Cell* Biol. 10:290, 2000.
Sester et al., "Rapid whole blood analysis of virus-specific CD4 and CD8 T cell responses in persistent HIV infection," *AIDS*, 14:2653-60), 2000.

* cited by examiner

*Primary Examiner*—Amy E Juedes
(74) *Attorney, Agent, or Firm*—Fulbright & Jaworski

(57) ABSTRACT

The invention relates to a method for infiltration of polypeptides in cells. The invention further relates to the use of the cells and urea-adjuvated polypeptides for the diagnosis, treatment or prevention of diseases. The invention further relates to the detection of polypeptide-specific immune cells.

10 Claims, 15 Drawing Sheets

Figure 1:
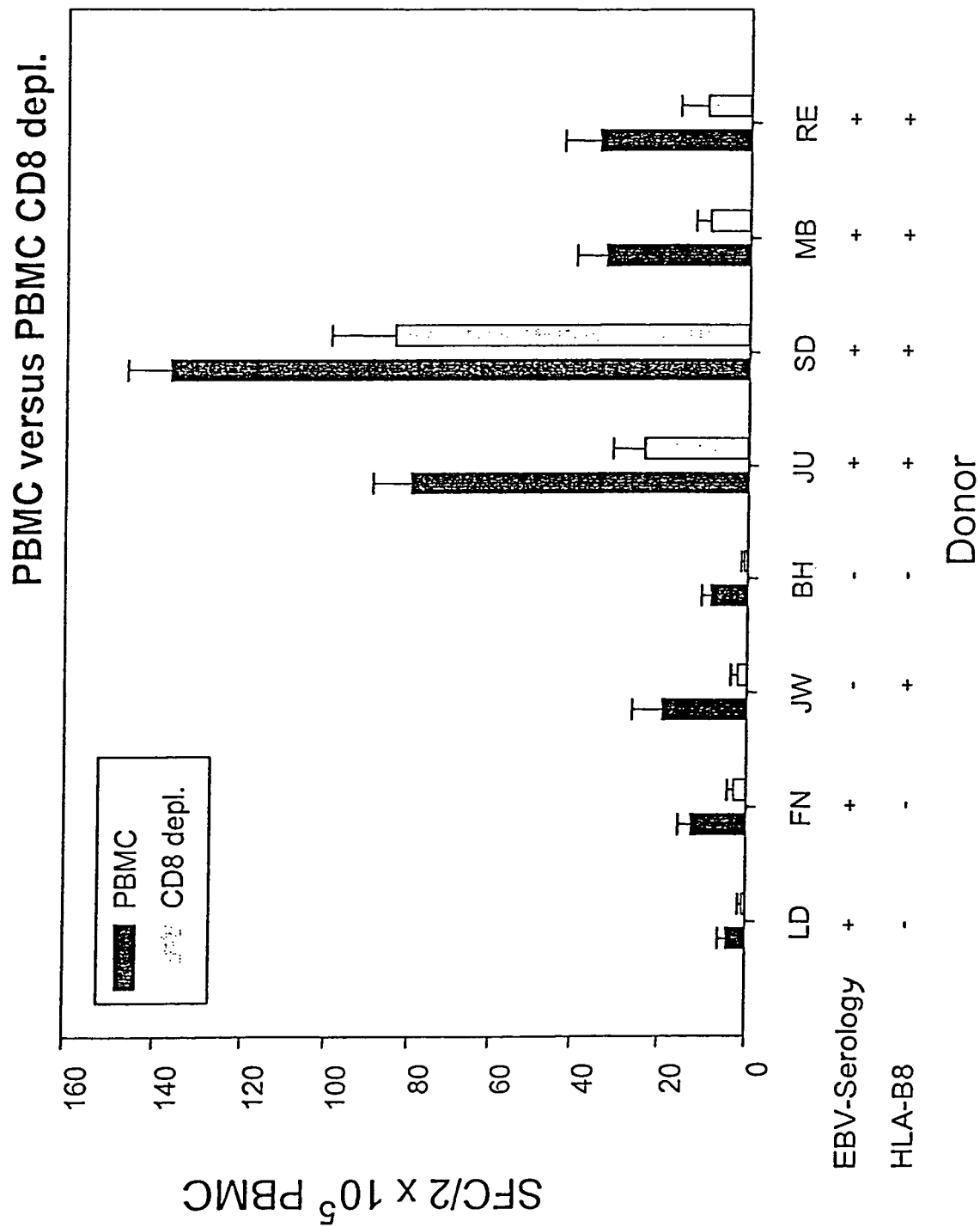

| Marker | Events | % Gated | % Total |
|---|---|---|---|
| All | 27845 | 100.00 | 26.48 |
| M1 | 1831 | 6.58 | 1.74 |
| M2 | 479 | 1.72 | 0.46 |

Gate: G1

| Marker | Events | % Gated | % Total |
|---|---|---|---|
| All | 28191 | 100.00 | 26.97 |
| M1 | 551 | 1.95 | 0.53 |
| M2 | 343 | 1.22 | 0.33 |

| Marker | Events | % Gated | % Total |
|---|---|---|---|
| All | 9108 | 100.00 | 8.66 |
| M1 | 292 | 3.21 | 0.28 |
| M2 | 8 | 0.09 | 0.01 |

Gate: G3

| Marker | Events | % Gated | % Total |
|---|---|---|---|
| All | 13273 | 100.00 | 12.70 |
| M1 | 511 | 3.85 | 0.49 |
| M2 | 337 | 2.54 | 0.32 |

Gate: G4

| Marker | Events | % Gated | % Total |
|---|---|---|---|
| All | 14222 | 100.00 | 13.53 |
| M1 | 1321 | 9.29 | 1.26 |
| M2 | 378 | 2.66 | 0.36 |

Gate: G4

| Marker | Events | % Gated | % Total |
|---|---|---|---|
| All | 13503 | 100.00 | 12.92 |
| M1 | 517 | 3.83 | 0.49 |
| M2 | 338 | 2.50 | 0.32 |

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Synthetic Primer

<400> SEQUENCE: 1
ggcggagatc tttagaaatt taagagatcc                30

<210> SEQ ID NO 2
<211> LENGTH: 30
<212> TYPE: DNA
<213> ORGANISM: Artificial Sequence
<220> FEATURE:
<223> OTHER INFORMATION: Synthetic Primer

<400> SEQUENCE: 2
ggcggggaat tcatgatgga cccaaactcg                                    30

<210> SEQ ID NO 3
<211> LENGTH: 8
<212> TYPE: PRT
<213> ORGANISM: Epstein-Barr Virus

<400> SEQUENCE: 3

Arg Ala Lys Phe Lys Gln Leu Leu
1               5

# USE OF UREA-ADJUVATED POLYPEPTIDES FOR DIAGNOSIS, PROPHYLAXIS AND TREATMENT

This application is the 371 national stage entry of PCT/DE 03/000917, filed on Mar. 19, 2003, the entire contents of which are hereby incorporated by reference.

The invention relates to a method for infiltration of polypeptides in cells. The invention further relates to the use of the cells and urea-adjuvated polypeptides for the diagnosis, treatment or prevention of diseases. The invention further relates to the detection of polypeptide-specific immune cells.

The acquired branch of the immune system consists of a humoral (immune globulins) and a cellular immune defence.

Cellular and pathogen-specific polypeptides are processed from antigen-presenting cells (APC) by specific cleavage and fragments (epitopes) thereof are presented together with MHC molecules of classes I and/or II on the cell surface. By means of their T-cell receptor, T cells specifically recognise epitopes presented in the complex with the endogenous MHC proteins and start an immune reaction.

T cells can be subdivided into different effector populations using specific surface proteins. $CD4^+CD8^-$ T-helper cells are of central importance in controlling the immune defence. According to a specific recognition of epitopes which are presented to them on the surface of APC together with MHC proteins, by secreting different messenger substances (for example, cytokines) they regulate the production of antibodies by B cells (humoral branch of the immune response) and the activation of $CD4^-CD8^+$ cytotoxic T cells (CTL) (cellular branch of the immune response).

The importance of $CD4^-CD8^+$ CTL lies in the recognition and destruction of cells and tissue which have degenerated and are affected by micro-organisms or parasites. T cells are thus an important protection mechanism of the acquired immune system for the prevention and control of microbial, especially virus-induced diseases, and for the recognition and destruction of degenerated endogenous cells. In addition to these T cell populations, another population of circulating T cells has been described by various working groups, which has a double positive $CD4^+CD8^{dim}$ phenotype.

$CD4^+CD8^{dim}$ T cells express $CD8\alpha\alpha$ homodimers and can be detected with a lower frequency (less than 2% of the total population of $CD3^+$ T cells) in the blood. A transient or persistent expansion of $CD4^+CD8^{dim}$ T cells was observed both in healthy persons and also in probands with various diseases, including infections with different viruses, for example, the human immune deficiency virus type 1 (HIV-1) and the human cytomegalovirus (HCMV) as well as patients with various autoimmune diseases.

Furthermore, other populations of antigen-specific T cells, the so-called $CD56^+CD8^+$ and $CD56^-CD57^+CD8^+$ NKT cells have been described. These cell populations express both a T cell receptor and also classical NK cell markers and can also be detected with lower frequency (2 to 5% or 5 to 10%) in peripheral blood mononuclear cells (PBMC). So far, only very little is known about the importance of these cell populations in the control of microbial infections and tumours.

Professional APC such as dendritic cells, monocytes, macrophages but also non-professional APC such as B cells play a central role both in the triggering of a T cell response to exogenous immunogens and in the induction of a T cell tolerance to endogenous tissue. The activation and proliferation of T cells takes place by the simultaneous triggering of two signals. The first signal is guided into the T cell by the T cell receptor which recognises the epitope in association with MHC on the surface of the APC.

The co-stimulatory signal is mediated by the specific interaction of the co-stimulatory molecules B7.1 (CD80) or B7.2 (CD86) on the APC with the relevant receptor (CD28) on the surface of the T cell. In the absence of the co-stimulatory signal, the epitope-specific T cell becomes anergic. Anergy describes a state in which the T cells cannot multiply and cannot respond to an antigen.

The condition of a polypeptide decisively determines the efficiency and route of the epitope processing and presentation by an APC. In addition, the degree of activation of an APC and thus the profile of the induced immune response is adversely influenced by the form of administration of a polypeptide. Thus, the concentration and biochemical properties of a polypeptide as well as the presence or absence of immune-modulatory substances (especially bacterial components such as lipopolysaccharides (LPS), nucleic acids (CpG-containing DNA) and polypeptides (e.g. flagellin)) are determining factors as to whether the cellular (T helper-1 (Th-1)-type mediated immunity) or humoral branch (T helper-2 (Th-2)-type mediated immune response) of the immune system is activated or whether the immune response proceeds tolerogenically.

Hitherto, only a very few methods for the incorporation of polypeptides into mammalian cells had been described.

Hitherto, for example, mechanical methods of microinjection and electroporation had been used with varying success for transferring protein into cells (Mi et al. (2000); Mol. Ther. 2:339; Schwarze et al. (2000); Trends Cell Biol. 10:290). Other methods for polypeptide transfer into cells are based on using protein transduction domains (PTD).

These amino acid sequences comprising 10 to 35 amino acids originate for example from the HIV Tat protein, the Herpes Simplex Virus (HSV) VP22 protein or Antennapedia. In addition, synthetic PTD sequences were determined by means of phage libraries. The membrane prevalence of polypeptides can be increased considerably by their coupling of these with PTD. Other methods described for protein transfer into cells are based on using various cationic lipid formulations or the incorporation of polypeptides in ISCOM® particles (CSL Limited, Victoria, Australia). All these methods are too work- or cost-intensive for routine use. In addition, many of the particular transfer systems possess cytotoxic (for example, liposomes) or modulatory properties (ISCOM® particles) which can subsequently adversely influence the natural properties of the treated cells.

Bearing in mind the importance of the cellular immune response for controlling microbial infections and tumours, many new strategies for the in vivo induction of epitope presentation on MHC class I and II proteins in immune cells are currently being tested. These include the use of (lipo-) peptides, (lipo-) proteins, particular immunogens, living attenuated bacteria and viruses, recombinant living vaccines (based on various recombinant bacteria and viruses) and DNA vaccines. Furthermore, ex vivo treated autologous APC which present specific peptides in the context with MHC proteins of classes I and II are a suitable reagent for the induction of polypeptide-specific immune responses, especially in therapeutic treatments. In earlier studies, APC pulsed with tumour extracts or cell lysates have proved suitable for simultaneously inducing $CD4^+$ and $CD8^+$ T cell responses (Herr et al. (2000), Blood, 96:1857).

At the present time, various methods are available for stimulating various populations of immune cells which are suitable to different extents for detecting specific populations of antigen-specific immune cells.

Direct loading of membrane-bound MHC proteins with peptides of defined length (optimally 8-11 amino acids for loading MHC class I proteins and optimally 10 to 20 amino acids for loading MHC class II proteins) is a method frequently used for stimulating defined populations of immune cells, especially $CD8^+$ cytotoxic cells (CTL) and $CD4^+$ T helper cells. However, important restrictions on the use of this stimulation method for the simultaneous measurement of different populations of immune cells lie in the fact that peptides of different size are specifically presented on MHC proteins of classes I or II whereby, when using defined peptides, it is not possible to simultaneously determine $CD4^+$ T helper cells and $CD8^+$ cytotoxic T cells. In addition, the specific recognition of T cell epitopes is subjected to an MHC restriction; that is, persons who express different MHC proteins recognise different epitopes within a polypeptide which makes the analysis of polypeptide-specific T cells in probands with variable MHC patterns considerably more difficult. Thus, only T cells which are directed against known epitopes in the context with defined MHC proteins can be specifically registered using this method.

In contrast, polypeptides produced recombinantly using various bacteria as well as insect, yeast or mammalian cells are suitable for detecting polypeptide-specific $CD4^+$ T helper cells regardless of the MHC restriction of the donor and the detailed knowledge of the T cell epitope localised in a polypeptide. However, recombinant polypeptides are almost exclusively taken up and recovered via the MHC class II processing and presentation route in APC so that this method is exclusively suitable for detecting $CD4^+$ T helper cells.

Furthermore, various methods for denaturing polypeptides have also been described which make it possible to supply these polypeptides to the MHC class I and MHC class II processing and presentation route. These methods include, for example, treatment of polypeptides with heat or sodium dodecyl sulphate (SDS). These methods proved to be suitable for achieving an epitope presentation on MHC class I and II molecules in murine APC (Schirmbeck et al. (1994), Eur. J. Immunol., 24:2068); (Schirmbeck et al. (1995), Vaccine, 13:857). In these studies it was shown that proteins denatured in various ways are taken up into the APC by means of various mechanisms and differ in terms of their efficiency for inducing a polypeptide loading of MHC class I polypeptides. Thus, compared with SDS-treated proteins, polypeptides treated using the heat inactivation method (1 hour at 60° C. or 15 min at 100° C.) only induced a slight stimulation of epitope presentation on MHC class I proteins in treated murine APCs. On the other hand, the SDS denaturing method proved to be little suited for use in human cell cultures because of the high toxicity.

Another method for stimulating the MHC class I and II presentation of epitopes on APC is based on the incorporation of polypeptides in particular structures, for example, liposomes, particular carrier substances, virus-like particles or lipoprotein particles. The first studies confirmed the suitability of HIV-1 $Pr55^{gag}$ virus-like particles for the diagnosis of $CD4^+$ T helper cells and CTL (Sester et al. (2000), AIDS, 14:2653-60). However, the production of particle-bound polypeptides is expensive and costly. Furthermore, these antigens are not suitable for the diagnosis of other immune cell populations, for example $CD4^+CD8^{dim}$ cytotoxic T cells, $CD56^+CD8^+$ and $CD56^-CD57^+CD8^+$ NKT cells.

Another method for stimulating the MHC class I and II presentation of epitopes on APC is based on the incorporation of polynucleotides coding for the desired polypeptides using plasmids, non-viral or viral vectors. A disadvantage of using plasmids for diagnostic purposes is the low efficiency of the nucleic acid transfer in APC using the hitherto available transfection methods, for example electroporation or lipofection. Viral or bacterial vectors frequently have significantly increased transfection rates of APCs compared to plasmids. However, these gene transfer systems are frequently not immunologically inert and modulate the capability of APC for epitope processing and presentation of polypeptides (Jenne et al. (2001), *Trends Immunol.*, 22:102-7). In addition, the use of these nucleic-acid-based methods is limited by the expensive and costly production of gene ferries. Furthermore, so far there are no examples of application relating to the suitability of these systems for the diagnostics of other immune cell populations, for example, $CD4^+CD8^{dim}$ cytotoxic T cells, $CD56^+CD8^+$ NKT and $CD56^-CD57^+CD8^+$ NKT cells.

The detection of the individual populations used after various populations of immune cells have been stimulated will be briefly described here. So far $CD4^+$ T helper cells have been detected by determining the cell proliferation or the messenger substances (cytokines) produced by T cells after a specific stimulation. The cell proliferation is usually detected using a proliferation assay by determining the radioactive isotope $^3H$ tritium incorporated in the DNA of proliferating cells. The cytokine production from $CD4^+$ T cells after a polypeptide-specific stimulation can be determined by means of a cytokine ELISA, an ELISPOT assay or by means of FACS technology by determining intracellular cytokines or secreted cytokines (FACS secretion assay).

Polypeptide-specific $CD4^-CD8^+$ cytotoxic T cells (CTL) have conventionally been detected by detecting their specific cytotoxic activity or the messenger substances (cytokines) produced by CTL after a specific stimulation, especially of interferon-$\gamma$ (IFN-$\gamma$). The cytotoxicity is usually detected by means of a classical chromium release test or adequate non-radioactive method in which the release of enzymes or ATP from target cells as a result of a specific lysis by the effector cell with cytotoxic properties is measured.

The cytokine production from $CD8^+$ T cells after an epitope-specific stimulation can be determined by means of a cytokine ELISA, an ELISPOT assay or by using FACS technology by determining intracellular cytokines or secreted cytokines (FACS secretion assay). IFN-$\gamma$ is usually used as a marker cytokine for the presence of CTL. So far, autologous APC which present CTL epitopes in conjunction with MHC proteins of class I on their surfaces, have been used, for example, to stimulate epitope- or polypeptide-specific CTL. The induction of an MHC class I mediated epitope presentation on APC has so far been mediated by incubating this with epitope-carrying peptides of suitable length (8 to 11 amino acids), by incubating with lipopolypeptides, particular polypeptides or polypeptides packed in particular structures, lysates of polypeptide-producing cells, apoptotic cells as well as vital but killed polypeptide-producing micro-organisms, especially recombinant viruses, bacteria or yeasts.

So far, polypeptide-specific $CD4^+CD8^{dim}$ cytotoxic T cells have been detected by determining the IFN-$\gamma$ production after a specific stimulation of cells in whole blood by means of inactivated virus particles, for example, gp120-depleted HIV-1 antigen (Reimmune™ in incomplete Freund's adjuvant) or purified cytomegalovirus (CMV) lysate (Advanced Biotechnologies, Columbia, Md.) (Suni et al. (2001), Eur. J. Immunol., 31:2512-20).

$CD56^+CD8^+$ and $CD56^-CD57^+CD8^+$ NKT cells possess a very limited T cell receptor repertoire, which suggests that this cell population can only recognise a limited number of MHC presented antigens. So far, no methods have been described for detecting NKT cells in the human system.

Dimer and tetramer technology are methods for detecting epitope-specific CD8+ cytotoxic T cells and CD4+ T helper cells. However, limitations of these methods for widespread use in T cell diagnostics are based on the very high costs for the manufacture of dimers and tetramers. In addition, dimer and tetramer technology has so far only been available for a limited repertoire of MHC types, especially for frequent MHC class I proteins, for example, HLA A2. In addition, this technique only allows the detection of defined epitope-specific T cells. T cell reactivities against multiple epitopes can only be determined using this method with a substantial expenditure of time and money.

The stimulation of peripheral blood cells with inactivated virus particles is so far the only method described for the stimulation and detection of CD4+CD8$^{dim}$ cytotoxic T cells.

These stimulants, however, contain a complex mixture of different viral and non-viral polypeptides as well as other partly immune-stimulatory virus components such as nucleic acids, lipids and sugars. It is thus not possible to precisely allocate the T cell reactivity determined to defined viral polypeptides.

It is thus the object of the present invention to provide a detection system with which polypeptide-specific or epitope-specific T cell and other immune cell populations can be detected simultaneously. It is further the object of the present invention to provide a new method for the infiltration of polypeptides into cells, especially APCs.

It is further the object of the present invention to provide a new method for inducing the MHC class I and II presentation of polypeptide-specific epitopes by means of APCs.

This object is solved by the subject matter defined in the claims.

The following figures are used to explain the invention.

FIG. 1 is a graphical representation showing the number of IFN-γ secreting T cells after incubating peripheral blood mononuclear cells (PBMC) with urea-adjuvated BZLF1 polypeptide. In each case 2×10$^5$ PBMC or CD8+ T-cell-depleted PBMC from respectively 2 HLA B8-negative, EBV-positive donors (LD, FN), one HLA B8-negative, EBV-negative donor (BH), one HLA B8 positive, EBV negative donor (JW), and 4 HLA B8-positive, EBV-positive donors (JU, SD, MB, RE) were sown in T cell medium in ELISPOT plates and incubated with 5 μg/ml urea-adjuvated BZLF1 polypeptide in each case for 24 hours. The number of IFN-γ secreting cells was then determined using ELISPOT. The values shown are means±standard deviation (SD) from 6 independent experiments.

Figure 2A:
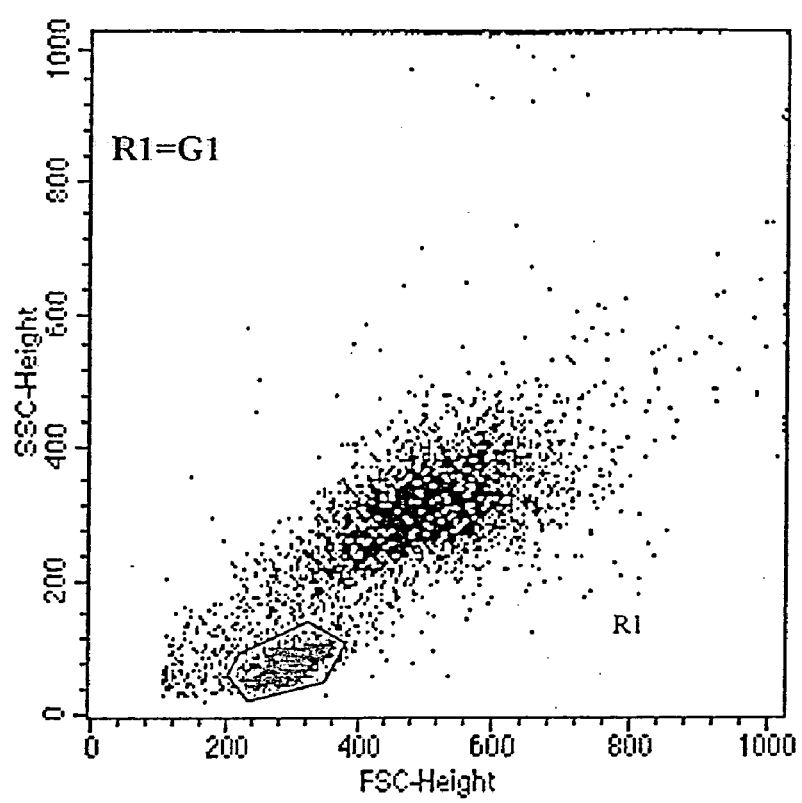

FIGS. 2a and b show the result of a flow-cytometric analysis of whole blood in a dotplot representation. An FSC/SSC (Forward Scatter/Side Scatter) dotplot is shown wherein the measurement region given by R1 (Region 1) corresponds to the lymphocyte population. In the following figures only the lymphocytes contained in G1 are shown. G1 corresponds to the population which was determined when restricting the measurement to one window in accordance with the region R1 in FIG. 2.

Figure 3A:
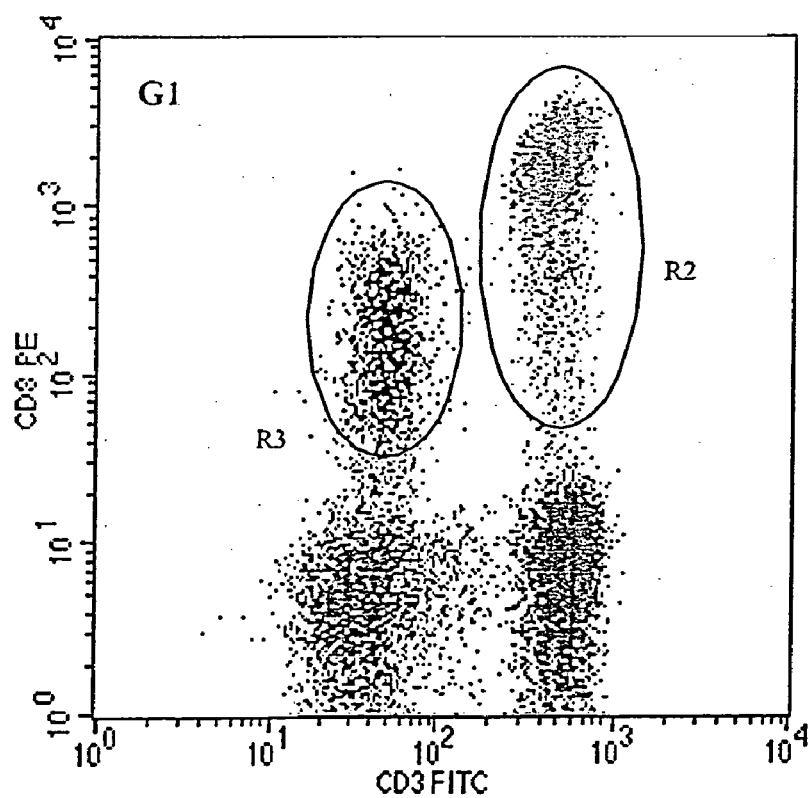
Figure 3B:
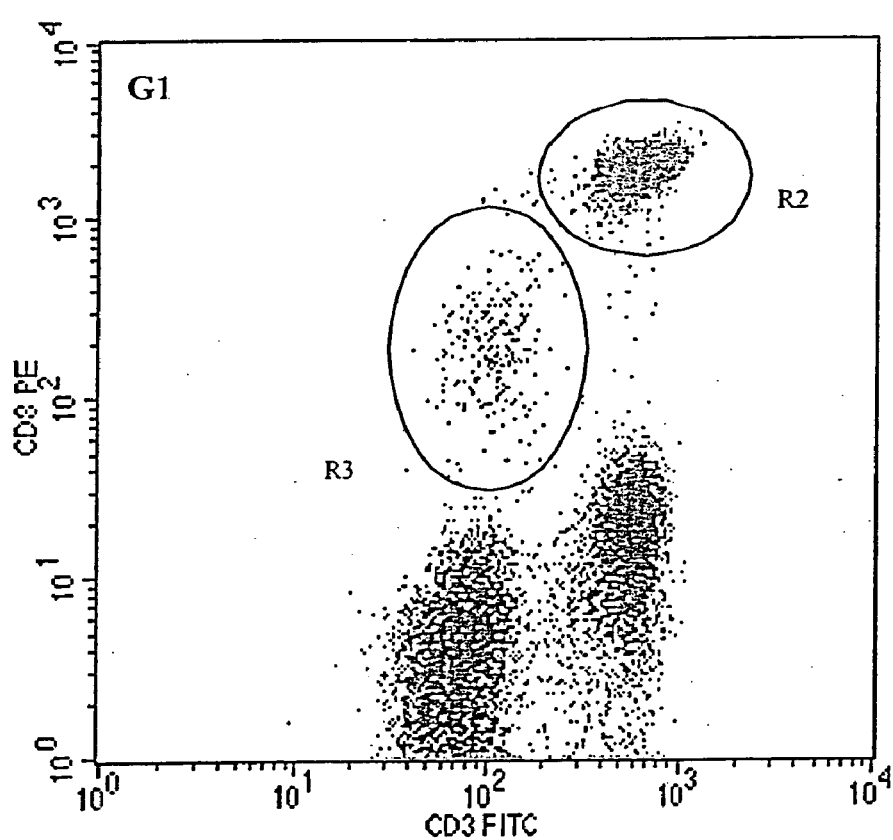

FIGS. 3a and b show dotplots giving the frequency and distribution of various populations of CD3 and CD8 positive lymphocytes in whole blood after stimulating with urea-adjuvated BZLF1 polypeptide (FIG. 3a) or a synthetic BZLF1 peptide (RAKFKQLL; Bogedain et al. (1995); J. Virol. 69:4872) (FIG. 3B), which contains a known CTL epitope.

Whole blood from an HLA B8-positive Epstein Barr Virus (EBV)-positive donor was either treated with urea-adjuvated BZLF1 protein or with the synthetic BZLF1 peptide and stimulated for 6 hours. The activated cells were then stained with anti-CD3-FITC and anti-CD8-APC. Two distinct populations of CD3+CD8+ cells can be detected by this method. The populations showing a strong expression of CD3 and CD8 polypeptides (shown in Region 2 (R2)), involve classical CD8+ cytotoxic T lymphocytes. The cell population shown in Region 3 (R3) which has a reduced expression of CD3 and CD8 polypeptides comprises CD56+ NKT cells, as confirmed in FIG. 5. In this case, the urea-adjuvated BZLF1 polypeptide (FIG. 3a) and the synthetic BZLF1 peptide (FIG. 3b) clearly differ in their capacity to stimulate both populations of CD3+ CD8+ cells.

Figure 4A:
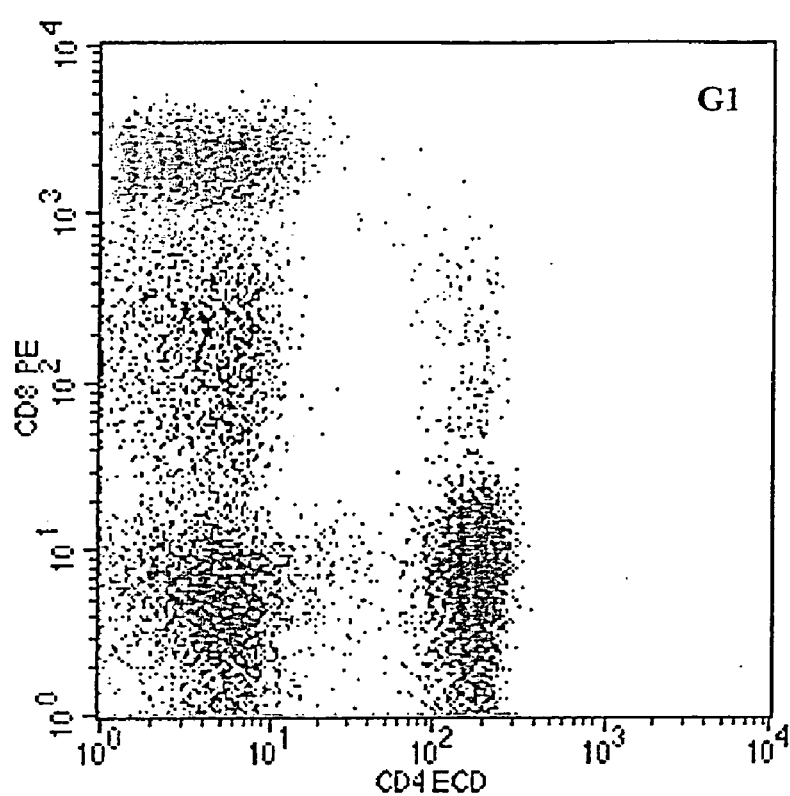
Figure 4B:
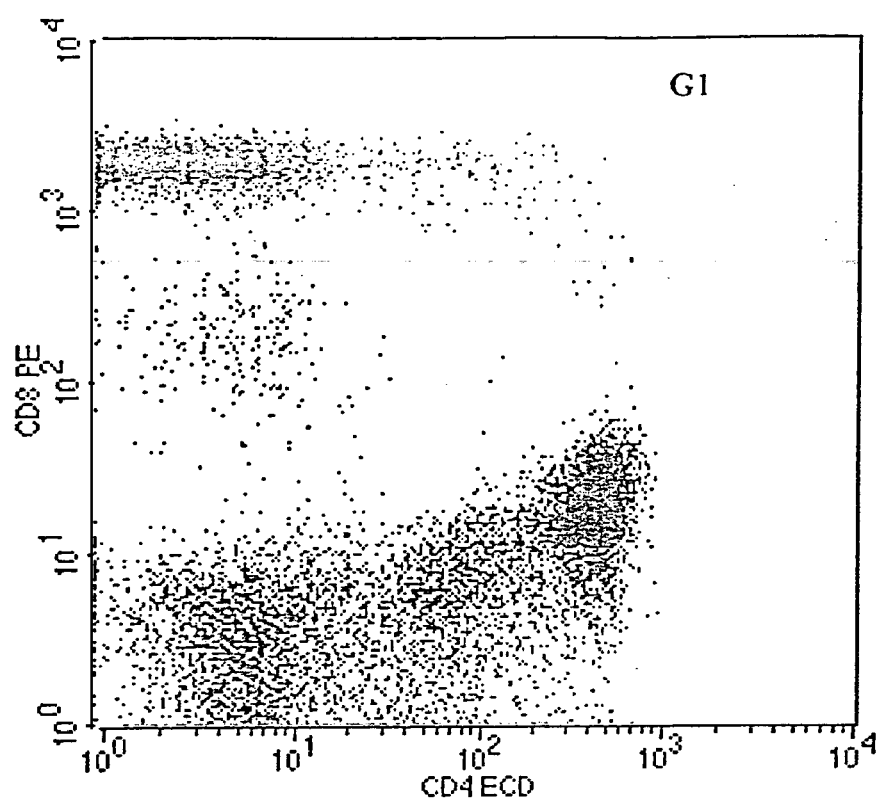

FIGS. 4a and b show dotplots giving the frequency and distribution of various populations of CD4+ and CD8+ lymphocytes in whole blood after stimulation with urea-adjuvated BZLF1 polypeptide (FIG. 4a) or a synthetic BZLF1 peptide (FIG. 4B), which contains a known CTL epitope. Whole blood from an EBV-positive donor was treated either with urea-adjuvated BZLF1 protein or the synthetic BZLF1 peptide and stimulated for 6 hours. The activated cells were then stained with anti-CD4-ECD and anti-CD8-APC. A population of CD4 and CD8 double positive CD4+CD8$^{dim}$ T-lymphocytes can be detected using this method. After re-stimulating the whole blood of an EBV-positive patient with urea-adjuvated BZLF1 polypeptide (FIG. 4a), a significantly increased number of these double-positive CD4+CD8$^{dim}$ cells could be detected compared with that after stimulating the same whole blood using the BZLF1 peptide (FIG. 4b).

Figure 5A:
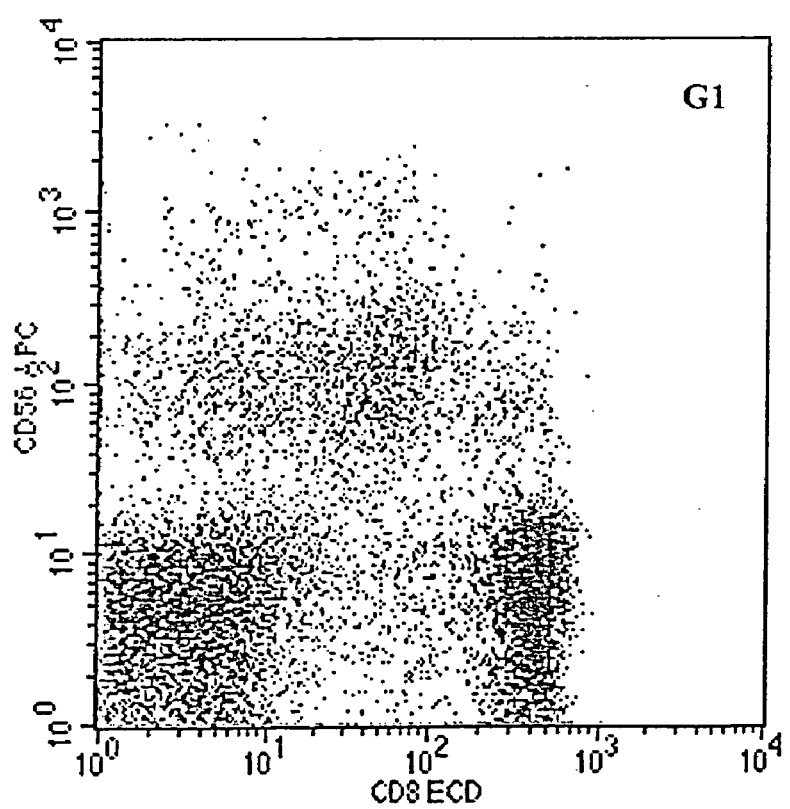
Figure 5B:
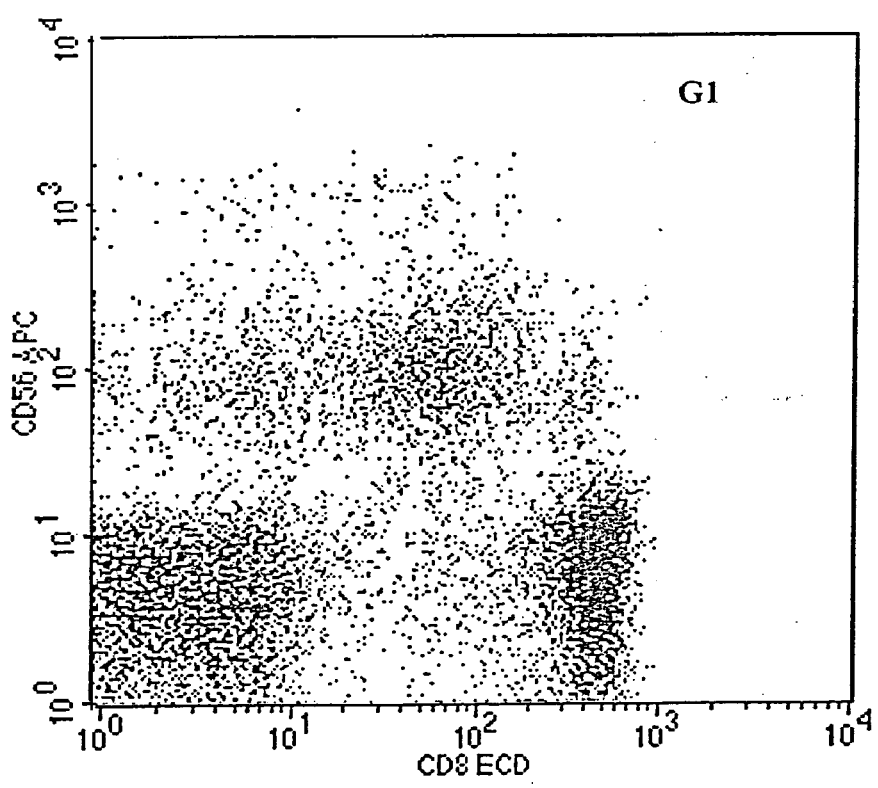

FIGS. 5a and b show dotplots giving cell populations which exhibit expression of the surface markers CD8 and CD56. It can be clearly seen in both figures (FIGS. 5a and 5b) that the population of CD8-positive cells, characterised in FIG. 2 by R3, and shown in blue here, expresses CD56 on the cell surface. Thus, the cells shown in the region R3 represent the population of the NKT cells.

Figure 6A:
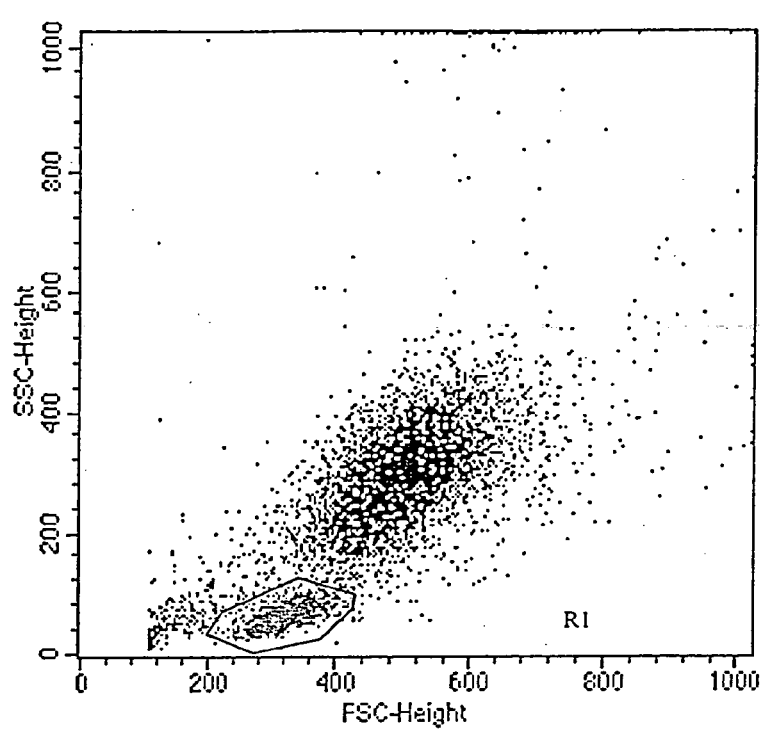
Figure 6B:
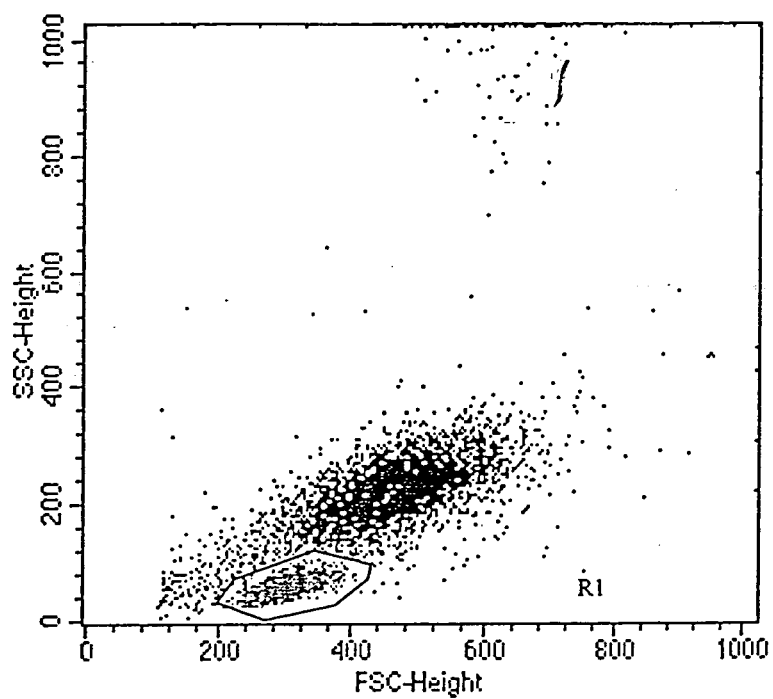

FIGS. 6a and b show dotplots giving the result of a flow-cytometric analysis of cells from whole blood after stimulating with urea-adjuvated BZLF1 polypeptide (FIG. 6a) or a synthetic BZLF1 peptide (FIG. 6B). This is a FSC/SSC (Forward Scatter/Side Scatter) dotplot, wherein the measurement region given by R1 (Region 1) represents the lymphocyte population.

Figure 7A:
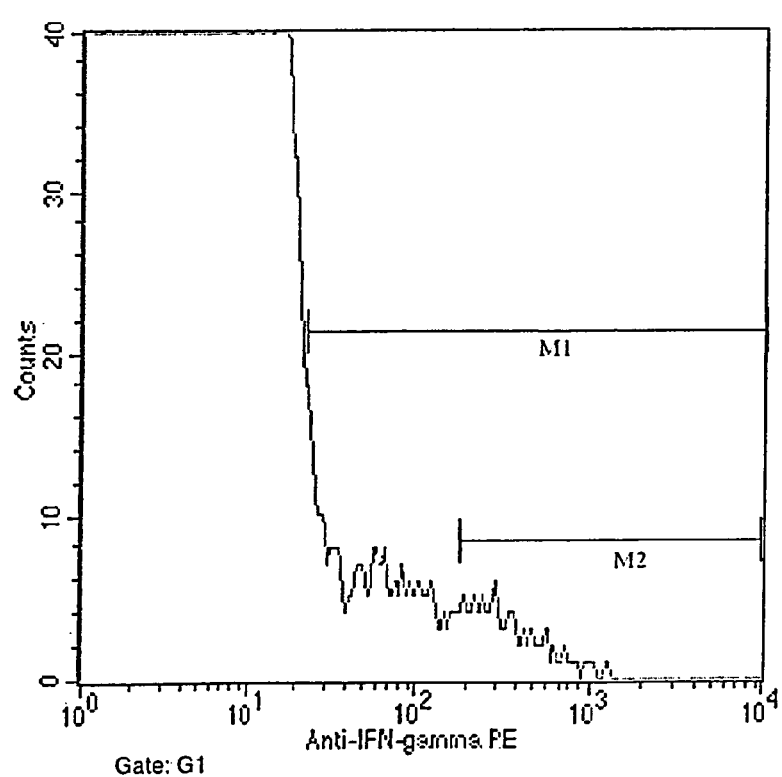
Figure 7B:
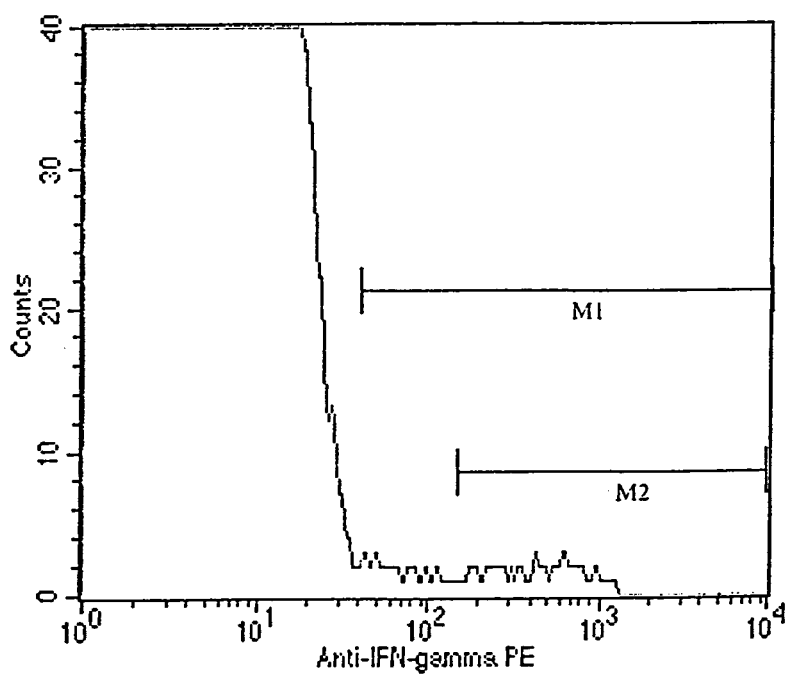

FIGS. 7a and b show histogram plots giving the result of the IFN-γ expression from various populations of the total lymphocytes registered in R1 after stimulation with urea-adjuvated BZLF1 polypeptide (FIG. 7a) or BZLF1 peptide (FIG. 7B). M1 and M2 are set as markers here. M1 designates the region in which the IFN-γ expression is to be classified as positive. All cells localised to the left of the characterised region M1 were non-specifically stained by non-specific binding of the anti-IFN-γ antibody within the cells. The region characterised by M2 shows the IFN-γ expression by the pure population of CD3+CD8+ cytotoxic T cells. The difference in the IFN-γ values shown in M1 and M2 characterises the IFN-γ production by weakly CD8+ cells with NK cell properties. After re-stimulation with urea-adjuvated BZLF1 polypeptide (FIG. 7a), compared with peptide stimulation, a significantly increased IFN-γ production from cells of whole blood as well as increased stimulation of the population of weakly CD8+ cells with NK cell properties can be observed.

Figure 8A:
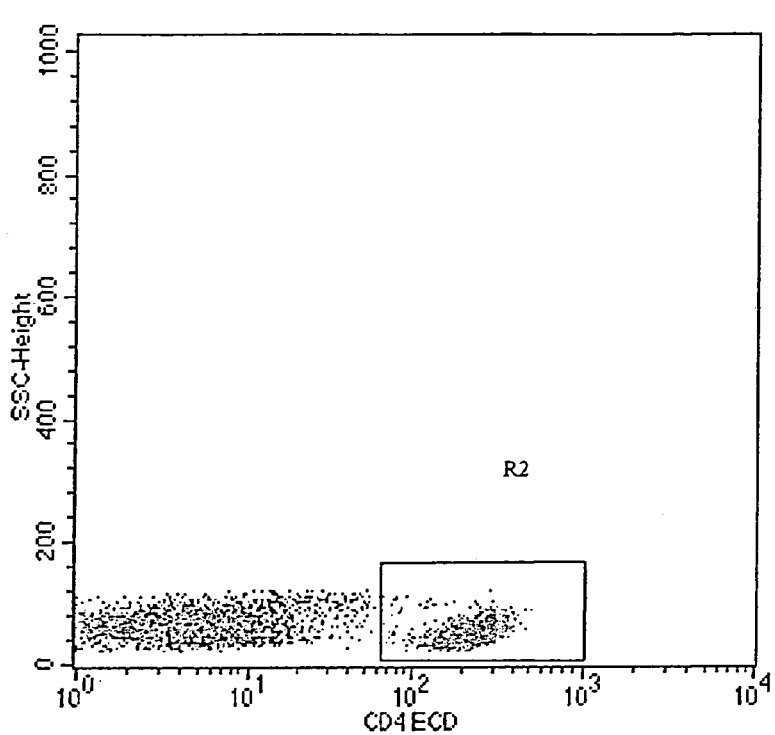
Figure 8B:
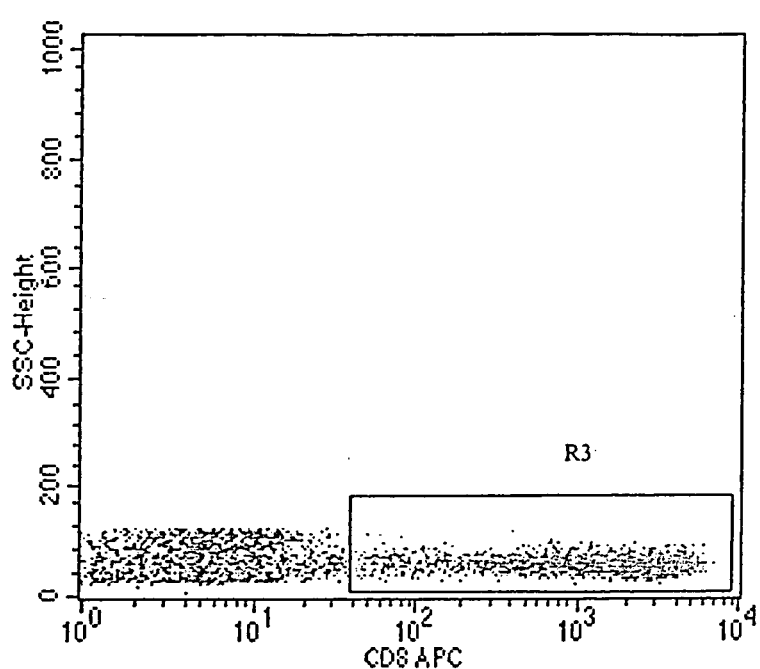

FIGS. 8a and b show dotplots giving the result of the expression of the surface marker CD8 against the side scatter (granularity of the cells) of cells from whole blood after stimulation with urea-adjuvated BZLF1 polypeptide (FIG. 8a) or the synthetic BZLF1 peptide (FIG. 8b). With this adjustment CD8+ cytotoxic T lymphocytes can be shown. These cells are designated here as the R3 population.

Figure 9A:
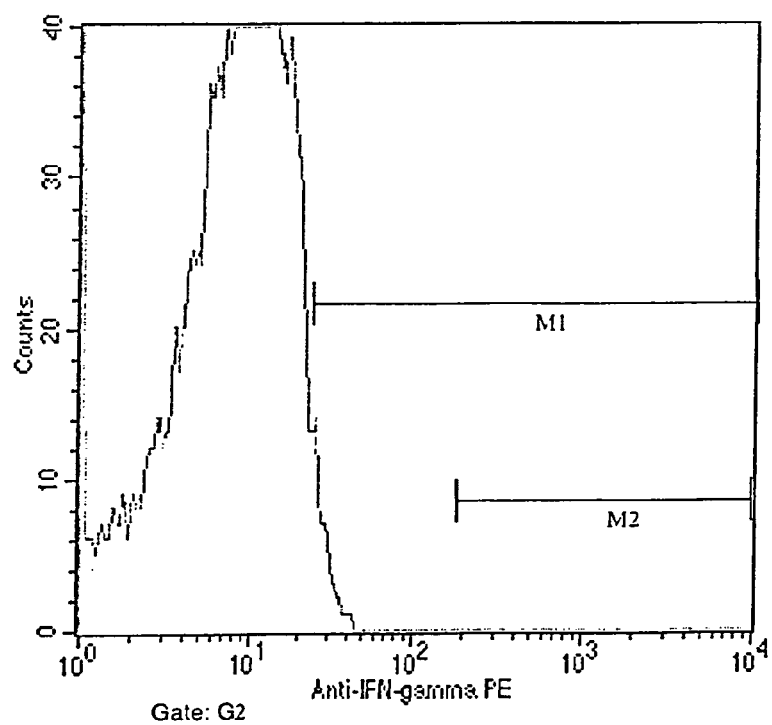
Figure 9B:
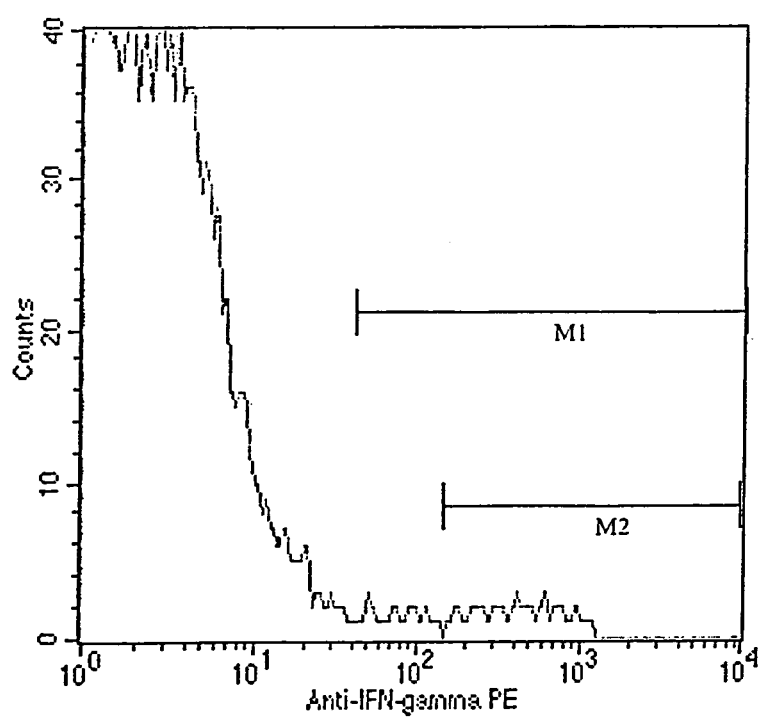

FIGS. 9a and b show histogram plots giving the result of the IFN-γ expression of the population of CD8$^+$ cytotoxic T cells from whole blood shown in R3 after stimulation with urea-adjuvated BZLF1 polypeptide (FIG. 9a) or the synthetic ZLF1 peptide (FIG. 9b). The markers M1 and M2 are set as in FIGS. 7a and b. This figure shows that urea-adjuvated BZLF1 protein and the synthetic BZLF1 peptide are equally suitable for determining BZLF1-specific cytotoxic T cells. However, CD4$^+$CD8$^{dim}$ and CD8$^+$ T cells could only be read out simultaneously after incubating the cells with urea-adjuvated BZLF1 polypeptide.

Figure 10A:
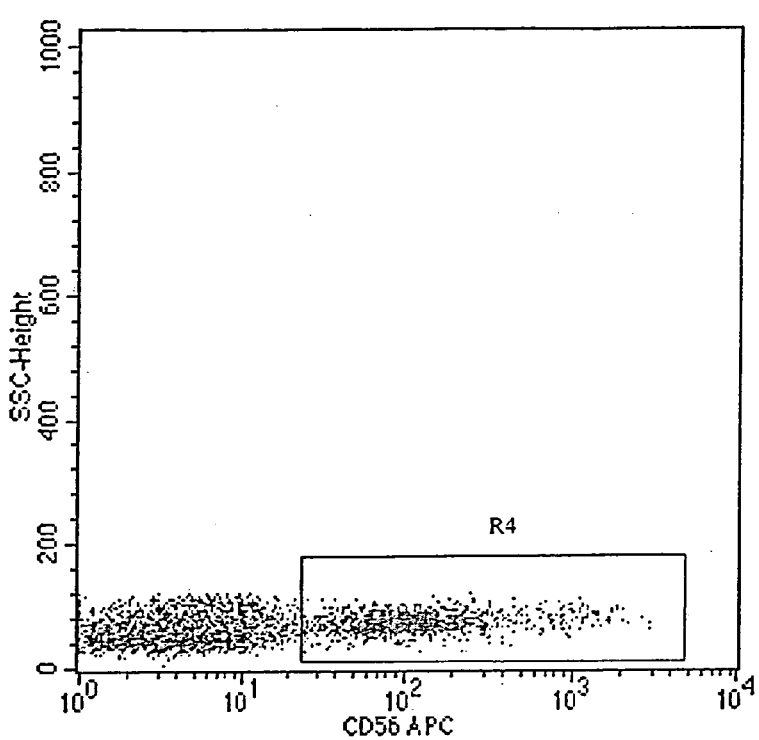
Figure 10B:
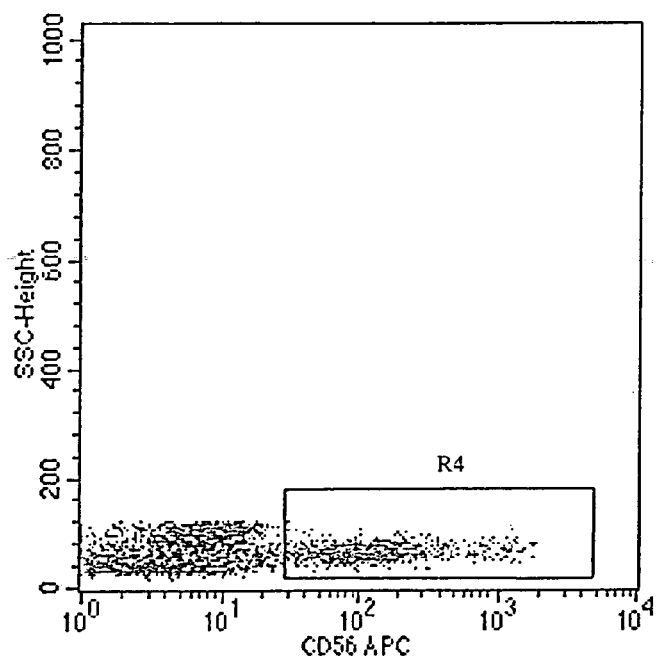

FIGS. 10a and b show dotplots giving the result of the expression of the surface marker CD56 against the side scatter of cells from whole blood after stimulation with urea-adjuvated BZLF1 polypeptide (FIG. 10a) or the synthetic BZLF1 peptide (FIG. 10b). CD56$^+$ NKT cells can be shown using this method. This population is designated here as R4.

Figure 11A:
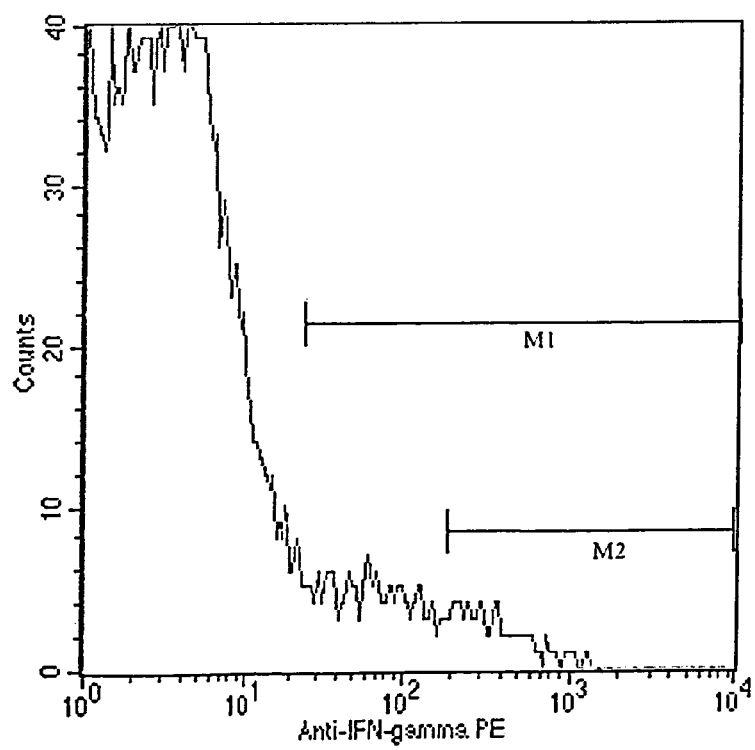
Figure 11B:
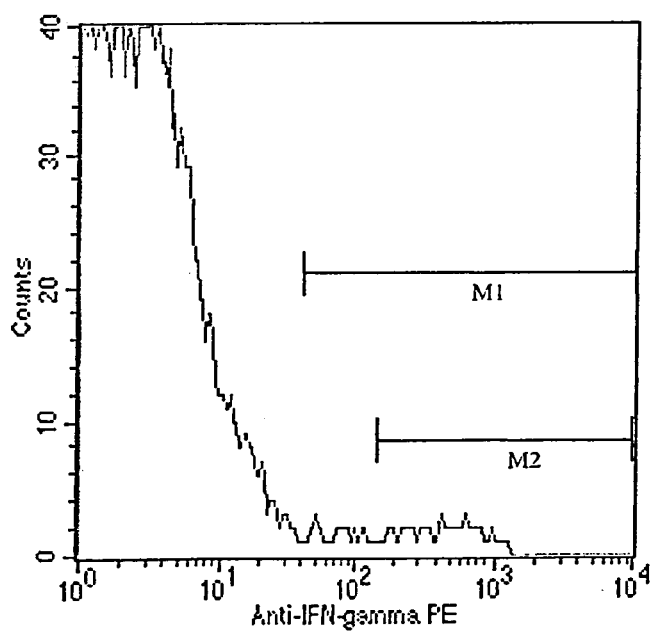

FIGS. 11a and b show histogram plots giving the result of the IFN-γ expression of the NKT cell population designated as R4 after stimulation with urea-adjuvated BZLF1 polypeptide (FIG. 11a) or the synthetic BZLF1 peptide (FIG. 11b). The markers M1 and M2 are set as in FIGS. 7a and b. This figure confirms the efficient stimulation of weakly CD8 positive NKT cell populations using urea-adjuvated BZLF1 polypeptide.

Figure 12:
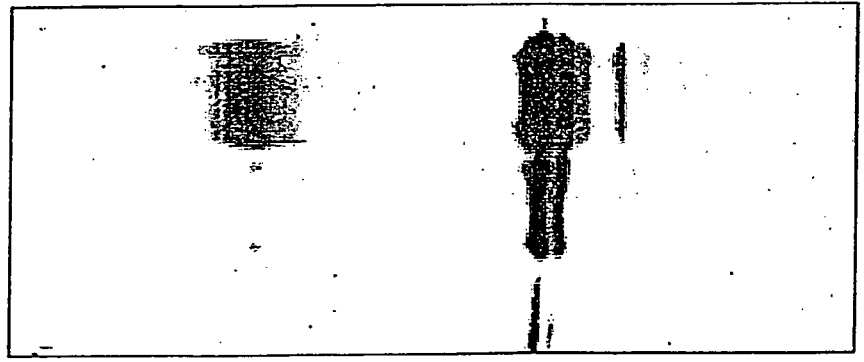
Figure 12:
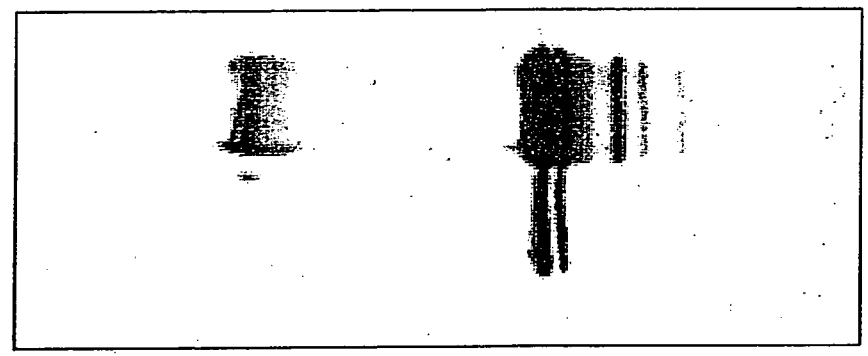
Figure 12:
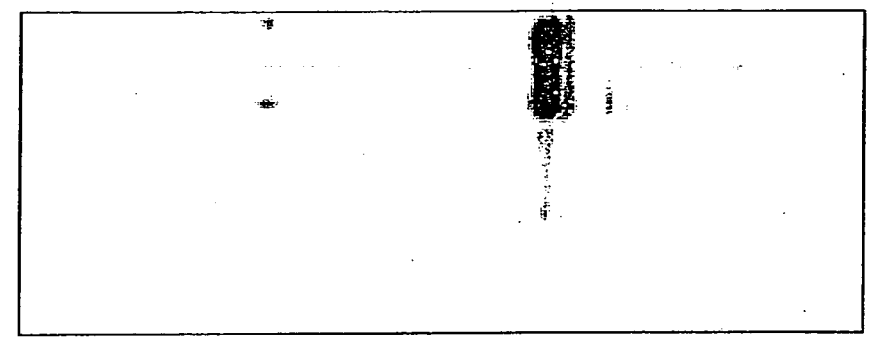

FIG. 12 shows an immunoblot giving the result of the reactivity of a polyclonal rabbit serum against recombinant BZLF1 protein. A rabbit was injected intramuscularly with 30 μg of urea- and Hunters Titermax adjuvated BZLF1 polypeptide and re-immunised with the same immunogen after 4 and 8 weeks. After a further 3 weeks, serum of the animal in a dilution of (A) 1:2000, (B) 1:10000 and (C) 1:50000 in the immunoblot was tested for its reactivity towards recombinant BZLF1-protein in concentrations of (1) 20 ng, (2) 100 ng and (3) 500 ng.

Figure 13:
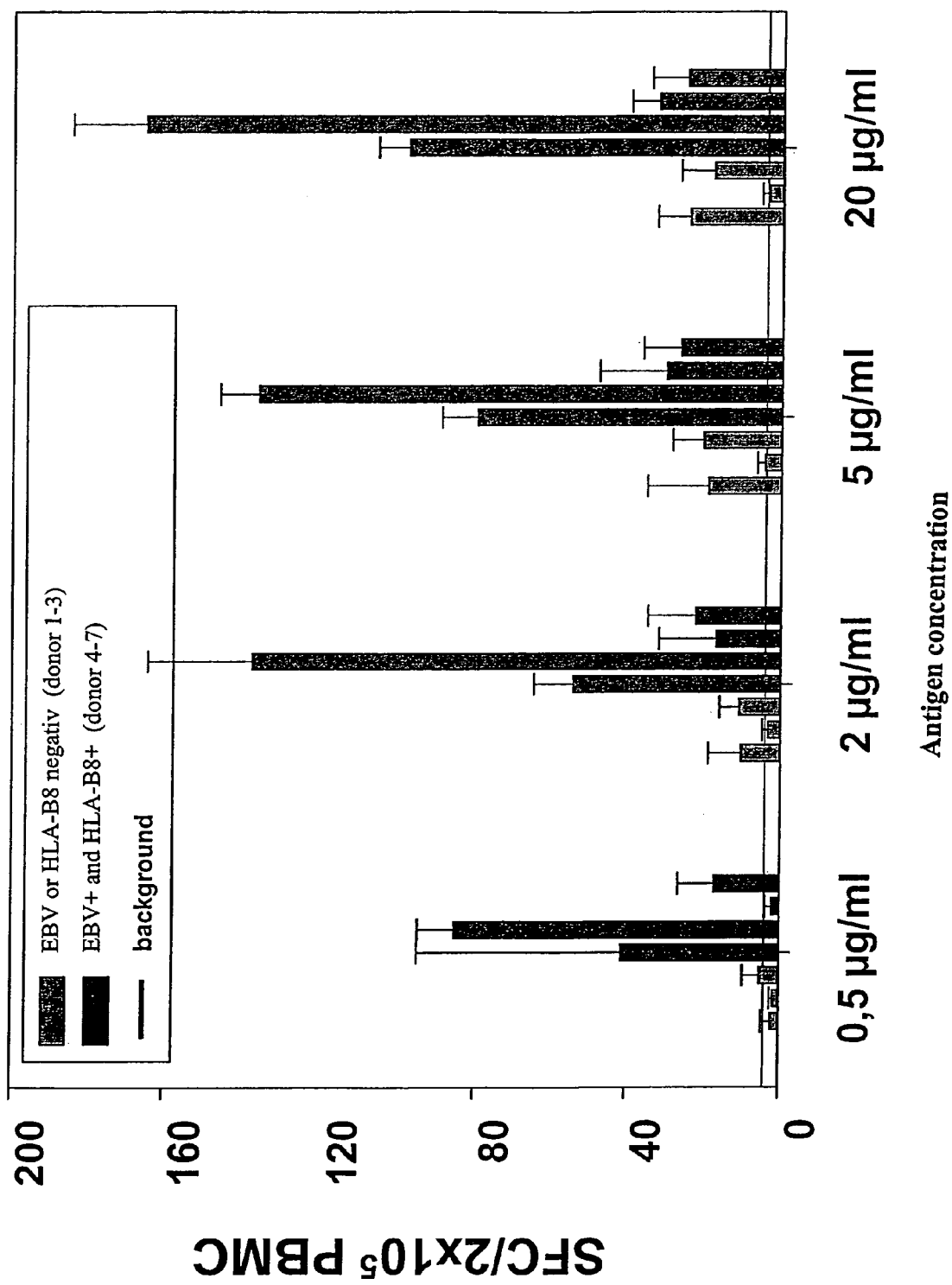

FIG. 13 is a schematic diagram showing the dose dependence of the IFN-γ secretion after stimulation with urea-treated BZLF-1 protein. The studies showed that BPMCs from 2 of the 4 tested HLA-B8-positive, EBV-positive donors at all the tested BZLF-1 concentrations showed a significantly increased number of IFN-γ producing BZLF-1-specific T cells compared to the negative controls (donors 1-3). In these experiments, low concentrations of urea-adjuvated BZLF-1 protein were sufficient to detect a significantly increased number of BZLF-1 specific, IFN-γ producing T cell compared to the negative controls (donors 1-3) in 3 out of 4 HLA-B8-positive, EBV-positive donors.

Figure 14:
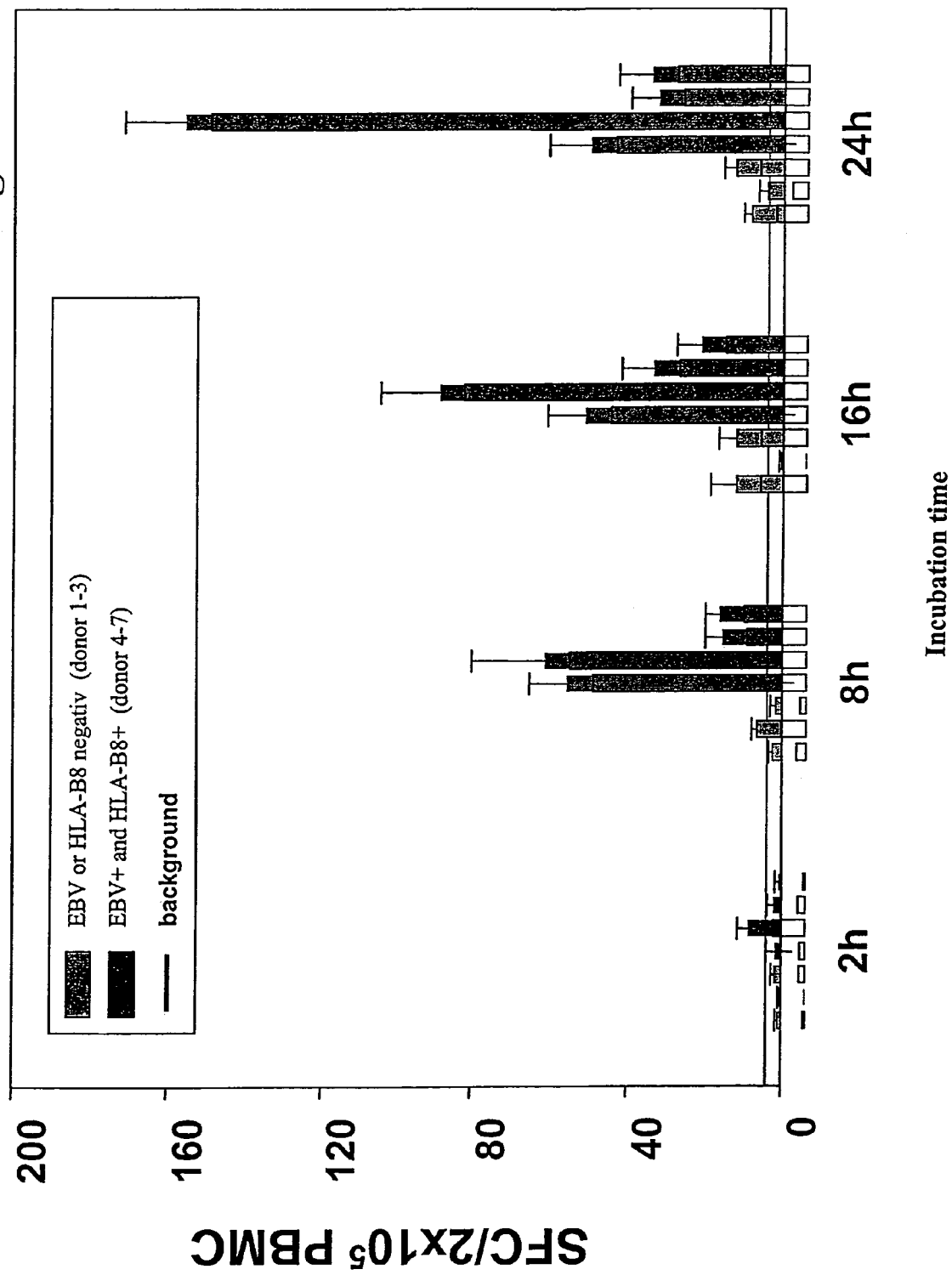

FIG. 14 is a schematic diagram showing the time behaviour of IFN-γ secretion after stimulation with urea-treated BZLF-1 protein. The studies showed that after incubation for 8 hours, all HLA-B8-positive, EBV-positive donors (donors 4-7) showed a significantly increased number of IFN-γ producing, BZLF-1-specific T cells compared to all the "control probands" (donors 1-3). The maximum number of IFN-γ producing cells could be observed after 16-24 hours depending on the donor.

Figure 15:
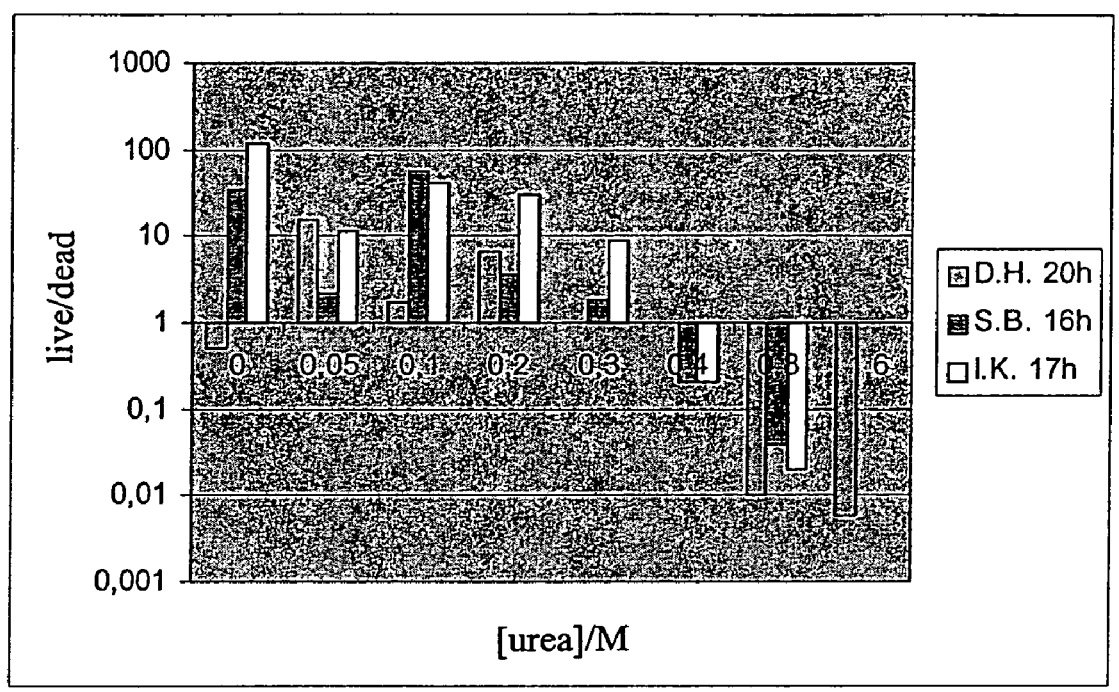

FIG. 15 is a graph showing the influence of the urea concentration on the vitality of PBMCs. D.H., S.B. and I.K. designate the donors.

Generally used abbreviations for nucleotides and amino acids are used in the present invention.

The term "genomic" used here denotes the entirety or fragments of the genetic material of an organism.

The term "polynucleotide" used here denotes the polymeric form of nucleotides of arbitrary length, preferably deoxyribonucleotides (DNA) or ribonucleotides (RNA). The term only denotes the primary structure of the molecule. The term includes double- and single-stranded DNA or RNA, e.g. decoy or antisense polynucleotides.

The term "polypeptide" used here denotes a polymer of amino acids of arbitrary length. The term polypeptide also comprises the terms epitope, peptide, oligopeptide, protein, polyprotein and aggregates of polypeptides. Also included in this term are polypeptides which have post-translational modifications e.g. glycosylations, acetylations, phosphorylations and similar modifications.

This term furthermore comprises, for example, polypeptides which have one or a plurality of analogs of amino acids (e.g. unnatural amino acids), polypeptides with substituted links as well as other modifications which are state of the art, regardless of whether they occur naturally or are of non-natural origin.

The term "urea-adjuvated" used here means that a molecule, e.g., a polypeptide is present in a solution, preferably an aqueous solution such as water, a buffer solution, a cell culture medium or a body fluid which has a certain urea concentration. The term "urea-adjuvated" thus means that the polypeptides are not only denatured by urea but are also brought in contact with cells for transfection in a urea-containing solution. The urea concentration of the denaturing and transfection solution can be identical or different. Furthermore, the urea solution can contain NaCl and/or DTE. The urea concentration of the transfection solution preferably has a final concentration in the range of about 0.001 to about 0.8 mol/liter, especially preferably in the range of about 0.001 to about 0.2 mol/liter, further from about 0.001 to about 0.1 mol/liter, especially preferably from about 0.001 to about 0.01 mol/liter, further especially preferably from about 0.01 to about 0.2 mol/liter, further from about 0.01 to about 0.1 mol/liter further especially preferably from about 0.1 to about 0.8 mol/liter. However, the urea concentration can also be less than 0.001 mol/liter or more than 0.8 mol/liter. If there is a high total number of living cells and a ratio of living to dead cells where the living cells predominate, the urea concentration of the transfection solution should be less than 0.3 mol/liter, preferably for example. 2.9, 2.8, 2.7, 2.6, 2.5 or any concentration less than 0.3 mol/liter.

The terms "purified", "purified" and "isolated" mean that a molecule, for example a polypeptide or a nucleic acid sequence is present in the completest possible absence of biological macromolecules of comparable type. The terms mean a fractional weight of the desired product of at least 75%, preferably of at least 85%, particularly preferably of at least 95% and especially preferably of at least 98% to the total weight of the biological macromolecules present (water, buffer and other small molecules, especially molecules having a molecular mass of less than 1000 are not included with the biological macromolecules).

The term "epitope" used here designates the region of a polypeptide which possesses antigen properties and for example serves as a recognition site of T cells or immunoglobulins. In the sense of this invention epitopes for example are those regions of polypeptides which are recognised by immune cells such as, for example, CD4$^+$ T helper cells, CD8$^+$ cytotoxic T cells, CD4$^+$CD8$^{dim}$ cytotoxic T cells, CD56$^+$CD8$^+$ and CD56-CD57$^+$CD8$^+$ NKT cells or CD4$^+$CD25$^+$ T suppressor cells. An epitope can comprise 3 or more amino acids. Usually, an epitope consists of at least 5 to 7 amino acids or, which is more common, 8-11 amino acids, or however of more than 11 amino acids, or however of more than 20 amino acids, even more rarely of more than 30 amino acids. The term "epitope" also comprises a unique spatial conformation for the epitope. This spatial conformation is obtained from the sequence of amino acids in the region of the epitope.

The term "micro-organism" used here designates viruses, prokaryotic and eukaryotic microbes, such as for example archaebacteria, single cells and fungi; the latter group for example comprises yeast and filamentous fungi.

The term "immune cells" used here denotes lymphocytes with regulatory or cytolytic properties such as, for example, $CD4^+$ T helper cells, $CD8^+$ cytotoxic T cells, $CD4^+CD8^{dim}$ cytotoxic T cells, $CD4^+CD25^+$ T suppressor cells, $CD56^+CD8^+$ and $CD56^-CD57^+CD8^+$ NKT cells as well as NK cells.

The term "antigen-presenting cell" (APC) used comprises cells which are capable of capturing, processing and presenting fragments of these polypeptides (epitopes) to the immune system in association with MHC class I and MHC Class II proteins. In particular, the term "antigen-presenting cell" comprises dendritic cells (Langerhans cells), monocytes, macrophages, B cells but also vascular epithelial cells and various epithelial, mesenchymal cells as well as microglia cells of the brain.

The present invention relates to a method for polypeptide transfer in cells, comprising the following steps:
a) Incubating polypeptides with a urea solution,
b) Incubating cells with the polypeptides present in the urea solution.

The polypeptides can be synthetically produced polypeptides or they can be expressed in various cells by means of usual pro- or eukaryotic expression systems, wherein the following list only contains a few cells as examples, e.g. bacteria such as *Bacillus subtilis, E. coli, Streptococcus cremoris* or *Streptococcus lividans*, yeast cells such as *Candida albicans, Candida maltosa, Hansenula polymorpha, Kluyveromyces fragilis, Saccharomyces cerevisiae, Schizosaccharomyces pombe*, or *Yarrowia lipolytica*, insect cells such as *Aedes aegypti, Autographa californica, Bombvx mori, Drosophila melanogaster, Spodoptera frugiperda*, or *Trichoplusia ni*, mammalian cells such as Chinese hamster ovary (CHO) cells, HeLa cells, baby hamster kidney (BHK) cells, monkey kidney cells (COS), or plant cells. Said systems for expression of polypeptides have been published many times and are state of the art.

The polypeptides used can be purified by conventional molecular biological methods, e.g. by cell disruption, nucleic acid digestion, methods for concentrating proteins, affinity chromatography, ion exchanger chromatography and gel filtration, or in combination with polypeptide-denaturing methods e.g. acid precipitation, urea treatment, alkali treatment, heat treatment, treatment with sodium dodecylsulphate (SDS) or sonification. These methods for purifying polypeptides can furthermore be combined in an arbitrary fashion.

The peptides can be synthetic i.e. non-naturally occurring polypeptides or they can occur in arbitrary living beings, e.g. in mammals such as humans, primates, mouse, rat, rabbit, sheep, cow, pig or in any animals, parasites, micro-organisms or viruses. However, they can also originate from plants and algae. In addition, they can originate from prion proteins.

The concentration of urea solution in step a) is preferably in the range of about 0.01 mol/liter to about 10 mol/liter or even higher, preferably up to about 0.1 mol/liter, particularly preferably in the range of about 0.1 to about 0.5 mol/liter, especially preferably in the range of about 0.5 to about 5 mol/liter, further especially preferably from about 5 to about 1.0 mol/liter or is more than 10 mol/liter.

The polypeptides can be used in any arbitrary concentrations, the concentration preferably lies in the range of about 0.01 to about 50 µg/µl or higher, preferably in the range of about 0.01 to about 0.1 µg/µl, particularly preferably from about 0.1 to about 0.5 µg/µl, especially preferably from about 0.5 to about 2 µg/µl, further especially preferably from about 2 to about 10 µg/µl or from about 10 to about 50 µg/µl or more than 50 µg/µl.

The incubation time of the polypeptides with the urea solution can be less than 10 seconds, or about 10 seconds up to one day, preferably about one minute, or about one minute up to about one hour, particularly preferably about one hour or more than one day. The polypeptides can furthermore either be stored frozen or at a temperature at which the urea solution is in the liquid state, for any arbitrarily long time in the urea solution, e.g., for more than one week, for more than one month or for more than one year.

The polypeptides present in the urea solution are then used for incubating the cells. Such a large volume of the polypeptide/urea solution to the cells is used that the concentration of polypeptides for approximately $10^6$ cells is in the range of about 0.1 to about 200 µg or higher, preferably in the range of about 0.1 to about 200 µg, particularly preferably from about 0.1 to about 2 µg, especially preferably from about 0.1 to about 10 µg, further especially preferably from about 10 to about 50 µg or from about 50 to about 200 µg of polypeptide.

The urea concentration in step b) should preferably have a final concentration in the range of about 0.001 to about 0.8 mol/liter, particularly preferably in the range of about 0.001 to about 0.2 mol/liter, further from about 0.001 to about 0.1 mol/liter, especially preferably from about 0.001 to about 0.01 mol/liter, further especially preferably from about 0.01 to about 0.2 mol/liter, further from about 0.01 to about 0.1 mol/liter, further especially preferably from about 0.1 to about 0.8 mol/liter. However the urea concentration can also be less than 0.001 mol/liter, or more than 0.8 mol/liter. If there is a high total number of living cells and a ratio of living to dead cells where the living cells predominate, the urea concentration in step b) should be less than 0.3 mol/liter, preferably, for example, 2.9, 2.8, 2.7, 2.6, 2.5 or any concentration less than 0.3 mol/liter. In addition, the urea solution can contain NaCl and/or DTE, wherein the concentration of NaCl is in the range of about 0.25 mmol/liter to about 0.2 mol/liter and that of DTE is in the range of about 0.25 nmol/liter to about 0.2 mmol/liter. Furthermore, the DTE concentration can be less than 0.25 nmol/liter or greater than 0.2 mmol/liter.

The polypeptide/urea solution is incubated with the cells for about 1 to about 240 hours or longer, preferably for about 2 to about 6 hours or for about 6 to about 12 hours or for about 12 to about 36 hours, or for about 36 to about 240 hours.

The method according to the invention can be used to infiltrate polypeptides into arbitrary cells, that is prokaryotic e.g. bacteria and eukaryotic cells, e.g. fungi such as yeasts and filamentous fungi, insect cells, bird, reptile, fish, amphibian, mammalian cells e.g., murine or human cells e.g. antigen-presenting cells.

In contrast to the methods described hitherto for polypeptide transfer in cells, the method according to the invention is especially distinguished by the fact that it is universally applicable, simple to implement with high efficiency and the cost is very low.

The cells treated using the method according to the invention can be used in the area of research, diagnostics and treatment and prevention of diseases in animals and humans. For example, the APCs obtained using the method according to the invention are suitable for prophylactic and therapeutic applications for combating infectious diseases and tumours. Furthermore, the APCs obtained using the method according to the invention are suitable for the simultaneous diagnostics of a wide range of polypeptide-specific and immunogenstimulatable immune cells, comprising CD4$^+$CD8$^-$ T-helper cells, CD4$^-$CD8$^+$ cytotoxic T cells, CD4$^+$CD8$^{dim}$ cytotoxic T cells, CD4$^+$CD25$^+$ T-suppressor cells, CD56$^+$CD8$^+$ and CD56$^-$CD57$^+$CD8$^+$ NKT-cells or CD56$^+$ NK cells. Thus, the invention further relates to cells obtained using the method according to the invention and their use.

A further aspect of the present invention relates to the use of urea-adjuvated polypeptides in a plurality of different scientific, medicinal and diagnostic applications, e.g. for studying the importance of these polypeptides in cellular processes, for inducing humoral and cellular immune responses in experimental animals and in humans, for (a) obtaining sera and antibodies for diagnostic, therapeutic and preventive applications, (b) for inducing suitable immune responses to protect against or for the treatment of microbial infections and tumour diseases, as (c) prophylactic and therapeutic vaccines or (d) for the ex vivo stimulation of APC for diagnostic, therapeutic and preventive purposes.

Thus, the present invention relates to the use of urea-adjuvated polypeptides for inducing specific antibodies and T-cells in animals, especially in mammals, e.g., in mice, rats, rabbits, sheep, horses, cattle, pigs, dogs, cats and primates. The urea-adjuvated polypeptides can also be used for inducing humoral and cellular immune responses in humans. In this case, the urea-adjuvated polypeptides can either be administered alone or in combination with immune-stimulating agents ("adjuvants").

Especially suitable adjuvants for enhancing the efficiency of the vaccines/vaccine combinations described include, for example: (1) gel-like adjuvants such as aluminium salts (Alum), such as aluminium hydroxide, aluminium phosphate, aluminium sulphate and calcium phosphate; (2) microbial adjuvants such as bacterial nucleic acids with CpG motifs, endotoxins such as, for example, monophosphoryl lipid A, exotoxins such as for example, the diphtheria, cholera, tetanus toxoid, the heat-labile enterotoxin of E. coli and muramyl dipeptides such as, for example, MDP; (3) oil emulsions and emulsion-based vaccines such as, for example, incomplete Freund's adjuvant (IFA), MF59, SAF and Ribi™ adjuvant system (RAS), (Ribi Immunochem, Hamilton, Mont.); (4) particular adjuvants such as, for example, immune-stimulatory complexes (ISCOMs), liposomes, PLG polymers, biologically degradable microspheres and saponins (QS-21), and synthetic adjuvants such as non-ionic block polymers, muramyl peptide analogues, polyphosphazene and synthetic polynucleotides and (5) cytokines, such as for example interleukins (IL-1, IL-2, IL-12 among others), granulocyte/macrophage colony-stimulating factor (GM-CSF) or macrophage colony stimulating factor (M-CSF), as well as the tumour necrosis factor (TNF). In addition to adjuvants, all other substances which have an immune-stimulating effect to enhance the efficiency of the vaccine compositions described can be used. A listing of suitable available adjuvants has been compiled, for example, by F. R. Vogel and can be retrieved via the world wide web at the following address www.niaid.nih.gov/aidsvaccine/pdf/compendium.pdf.

The vaccine combinations described (e.g., urea-adjuvated polypeptides in conjunction with a pharmaceutically accepted carrier component and/or an adjuvant) are added to the dilution solutions, such as for example, water, salt solutions, glycerol, ethanol. In addition, additional accessory components such as moistening and emulsifying agents, pH-buffering substances and similar components can be present in these compositions.

These vaccine combinations are usually present in injectable form, either as liquid solutions or suspensions.

The immunogen composition can equally be emulsified or incorporated in liposomes in order to achieve enhanced adjuvant properties in the sense of a pharmaceutically accepted carrier component. The vaccine composition can be administered by suitable administration routes. Possible among others in this case are oral, topical, intravenous, intraperitoneal, intramuscular, intra-articular, subcutaneous, intranasal or intradermal administration routes. The vaccine composition is used in the appropriate dosage for the indication. The determination of an appropriate dosage for various organisms is state of the art. The vaccine combinations described can either be used prophylactically or therapeutically. Furthermore, APC modified using urea-adjuvated polypeptides are suitable for therapeutic and preventive applications. Methods for obtaining and ex vivo expansion of APC, as well as for reinfusion of ex vivo modified APC in an organism have been published on many occasions and are state of the art.

A further aspect of the present invention relates to a method for detecting polypeptide-specific immune cells, comprising the following steps:
a) Incubating polypeptides with a urea solution,
b) Incubating APC-containing cell cultures or body fluids with the polypeptides present in the urea solution,
c) Incubating the APC-containing cell cultures or body fluids obtained according to step b) with immune cells or immune-cell-containing body fluids,
d) Simultaneously detecting and/or quantifying various subtypes of immune cells which are specific against the polypeptides from step a).

Step a) of the method according to the invention is identical to step a) of the method for polypeptide transfer in cells so that the corresponding preceding explanations also apply to the method for detecting polypeptide-specific immune cells.

The polypeptides present in the urea solution are then used for incubating the APC-containing cell cultures or body fluids. Such a large volume of the polypeptide/urea solution to the cells is used that for approximately $10^6$ cells the concentration of polypeptides is in the range of about 0.1 to about 200 µg or higher, preferably in the range of about 0.1 to about 200 µg, particularly preferably from about 0.1 to about 2 µg, especially preferably from about 2 to about 10 µg, further especially preferably from about 10 to about 50 µg, or from about 50 to about 200 µg of polypeptide.

The urea concentration in step b) should preferably have a final concentration in the range of about 0.001 to about 0.8 mol/liter, particularly preferably in the range of about 0.001 to about 0.2 mol/liter, further from about 0.001 to about 0.1 mol/liter, especially preferably from about 0.001 to about 0.01 mol/liter, further especially preferably from about 0.01 to about 0.2 mol/liter, further from about 0.01 to about 0.1 mol/liter, further especially preferably from about 0.1 to about 0.8 mol/liter. However the urea concentration can also be less than 0.001 mol/liter, or more than 0.8 mol/liter. If there is a high total number of living cells and a ratio of living to dead cells where the living cells predominate, the urea concentration in step b) should be less than 0.3 mol/liter, preferably, for example, 2.9, 2.8, 2.7, 2.6, 2.5 or any concentration less than 0.3 mol/liter. In addition, the urea solution can contain NaCl and/or DTE, wherein the concentration of NaCl is in the range of about 0.25 mmol/liter to about 0.2 mol/liter and that of DTE is in the range of about 0.25 nmol/liter to about 0.2 mmol/liter.

Furthermore, the DTE concentration can be less than 0.25 nmol/liter or greater than 0.2 mmol/liter.

The polypeptide/urea solution is incubated with the APC-containing cell cultures or body fluids for about 1 to about 240 hours or longer, preferably for about 2 to about 6 hours or for about 6 to about 12 hours or for about 12 to about 36 hours, or for about 36 to about 240 hours The APC-containing cell cultures can be purified PBMC population (leukapheresate), isolated monocytic cells or a separated APC population, e.g., dendritic cells (Langerhans cells), monocytes, macrophages or B cells. The term "APC-containing cell cultures" as used here thus means not only cells comprising APC held and multiplied in vitro in culture media but also cell populations taken from a proband, patients or an animal and containing purified APC.

The APC-containing body fluid is preferably whole blood or liquor.

For example, blood or another APC-containing body fluid can be taken from a proband or patient. The body fluid can either be used directly in step b) of the method according to the invention or APC-containing cell populations can be purified and then used. The purification of APC-containing cell populations from blood or other APC-containing body fluids is state of the art and known to the person skilled in the art.

After incubating the APC-containing cell cultures or body fluids with the polypeptides present in the urea solution, the cells are incubated with immune cells or immune-cell-containing body fluids. The immune cells or immune-cell-containing body fluids preferably come from the same proband, patient or animal from which the APC-containing cell cultures or body fluids originate. Alternatively, the immune cells or immune-cell-containing body fluids also come from probands, patients or animals having an MHC pattern compatible with the APC-containing cell cultures or body fluids.

The immune cells can be T cells, e.g., CD4$^+$ T cells, CD8$^+$ T cells, CD4$^+$CD8$^{dim}$ T cells, CD4$^+$CD25$^+$ suppressor T cells, but also other cell populations such as, for example, CD56$^+$CD8$^+$ and CD56$^-$CD57$^+$CD8$^+$ NKT cells or CD56$^+$ NK cells. Furthermore, the term immune cells also comprises an arbitrary mixture of CD4$^+$ T cells, CD8$^+$ T cells, CD4$^+$CD8$^{dim}$ T cells, CD4$^+$CD25$^+$ T cells, CD56$^+$CD8$^+$ as well as CD56$^-$CD57$^+$CD8$^+$ NKT cells and CD56$^+$ NK cells. The term "immune cells" as used here thus means not only immune cells held and multiplied in vitro in culture media but also immune cell populations taken from a proband, patient or an animal and purified. The immune-cell-containing body fluids are preferably whole blood or liquor. Methods for obtaining and purifying defined APC and immune cell populations have been published on many occasions and are state of the art.

The APC-containing cell culture or body fluid, e.g. whole blood, liquor or purified PBMC used in step b) can already contain the populations of immune cells to be detected. In this case, it is no longer necessary to add immune cells or immune-cell-containing body fluids in step c).

The incubation in step c) is about 1 to about 240 hours or longer, preferably about 2 to about 6 hours or about 6 to about 12 hours or about 12 to about 36 hours, or about 36 to about 240 hours under suitable cultivation conditions, for example, at 37° C. in a humidified atmosphere with 5 to 8% $CO_2$ in T cell medium (RPMI 1640 with 2 to 10% heat-inactivated (30 min, 56° C.) human serum or foetal calf serum (FCS), 2 mM glutamine and 100 mg/ml kanamycin or gentamicin (all components from PanSystems, Aidenbach)).

Other suitable conditions (variation of the media composition, temperature, air humidity, incubation time) for cultivating APC and immune cells have been described on many occasions and are state of the art.

The detection of defined populations of polypeptide-specific immune cells is based on the finding that after a specific recognition of polypeptides which are presented jointly with MHC proteins of classes II and/or I on the surface of APC, immune cells show an enhanced expression of characteristic cytokines, especially IFN-γ, or IL4 and/or IL5. As a result of a joint analysis of surface proteins which are characteristic of defined immune cell populations, and of cytokines, the presence and/or concentration of defined populations of polypeptide-specific immune cells can be detected from a mixture of different populations of immune cells. The detection and/or quantification in step d) thus takes place via the simultaneous detection of surface proteins and cytokines.

The detection of defined cell populations via specific surface proteins is carried out, for example via CD4 for T helper cells, CD8 for cytotoxic T cells, CD4 and CD8 for CD4$^+$CD8$^{dim}$ cytotoxic T cells, CD56 for NK cells, CD4 and CD25 for suppressor T cells, and CD56 and CD8 or CD57 and CD8 for various populations of NKT cells. Specific states of the cell populations (inactive versus activated cells versus memory cells) and the degree of activatability can furthermore be determined by detecting additional surface proteins (for example, CD69, CD45RA, CCR7) and intracellular proteins (for example, granzyme or perforin).

These characteristic surface markers for defined cell populations have been published on many occasions and the detection and characterisation of different populations of immune cells using FACS technology for example is state of the art.

The specific activation of immune cells is detected after incubating with the APC-containing cell cultures or body fluids obtained according to step b) by measuring any increased cytokine production of the activated immune cells. In this case, for example, CD4$^+$ T helper cells of the T-helper 1 type (Th-1), CD8$^+$ cytotoxic T cells, CD4$^+$CD8$^{dim}$ cytotoxic T cells, CD56$^+$ NK cells, and CD56$^+$CD8$^+$ or CD57$^+$CD8$^+$ NKT cells after specific stimulation produce increased IFNγ, whereas CD4$^+$ T helper cells of the T helper 2 type (Th-2) show increased production of the cytokines IL4 and IL5. The cytokines produced can be determined simply using methods published on many occasions either intracellularly or after secretion in the supernatant using, in some cases, commercially available methods, for example, using FACS technology. Detection is also possible by means of other cytokines produced after the specific activation of immune cells or other markers produced.

Reactive immune cells can be determined and characterised for example using Fluorescence activated cell scan (FACS) technology. This method allows the fluorescence intensity of individual cells in a mixed cell population to be measured using a flow cytometer. The flow-cytometric analysis of the cells is then made using an FACS system for example an FACS CALIBUR, Becton Dickinson (Franklin Lakes, N.J., USA), and the evaluation is made using the Cell Quest program (Becton Dickinson, Heidelberg).

Fluorescence-coupled, e.g. with R-phycoerythrin (R-PE), peridin-chlorophyll c (PerCP), fluoescein (FITC), Texas Red (TX), allophycocyanin (APC), Tandem PE-TX, Tandem PE-Cy5, PE-Cy7 or Tandem APC-Cy7, primary or secondary antibodies are suitable for detecting the characteristic surface proteins and cytokines described previously using FACS technology and are available commercially (for example, from Becton Dickinson, Dako, Coulter). In addition to the FACS method, other methods suitable for determining the production from immune cells, for example ELISA methods, Elispot methods and biosensors, are also suitable for detecting polypeptide specific immune cells. These methods for determining cytokines have been described on many occasions and are state of the art.

The method for detecting polypeptide-specific T cells according to the invention is suitable for many different scientific and medical applications, e.g. in analysis, diagnosis and therapy. Using the method according to the invention, different populations of polypeptide-specific immune cells can be identified at the same time, for example, for monitoring the efficiency of therapeutic and prophylactic vaccinations for inducing immune cells, for determining the efficiency of therapeutic treatments of diseases involving immune cells, for screening the safety and efficiency of medicaments which cause deletion of anergy of immune cells or bring about a general immune suppression, for monitoring and diagnosis of diseases induced by micro-organisms and parasites involving immune cells, for monitoring and diagnosis of chronic inflammations involving immune cells, for monitoring and diagnosis of tumour-antigen-specific immune cells, for monitoring and diagnosis of immune cells which play a role in transplant rejection, for the diagnosis of autoimmune diseases or for the specific selection of probands for vaccine trials and the testing of therapeutic treatments.

The method according to the invention is used in all vertebrates which have immune cells, especially T cells, especially in humans, primates and rodents. Polypeptide-specific immune cells can be detected and quantified for example from patients suffering from a microbial infection, a tumour disease, a chronically inflammatory disease, a transplant rejection or an autoimmune disease or however from healthy probands or participants of therapeutic or preventive trials. In addition, epitope-specific T cells can be detected using cells obtained by the method according to the invention, preferably using APCs obtained in primates or other animals which possess epitope-specific immune cells.

In contrast to the methods for the detection of polypeptide-specific immune cells described so far, the method according to the invention is characterised by the following advantages:

(1) Different populations of polypeptide-specific immune cells can be detected at the same time.
(2) The quantity and quality of different populations of polypeptide-specific immune cells can be detected at the same time.
(3) The method can easily be carried out using commercially available equipment (FACS) routinely used in many diagnostic laboratories.
(4) The method can be universally used to detect reactive polypeptide-specific immune cells regardless of the haplotype of the proband/patient.
(5) The diagnostic method according to the invention is suitable for the patient-specific determination of lymphocyte reactivity against a complex polypeptide. In this case, it is not necessary to know target epitopes of these immune cells to carry out the method.
(6) Compared to the conventional diagnostic methods (CT assay, ELISPOT, cytokine ELISA, proliferation assay), the method of detection for polypeptide-specific immune cells can be used universally, is easier to handle, significantly cheaper, less time-consuming and more sensitive.

The invention is explained using the following examples but is not restricted to these:

EXAMPLE 1

Production and Purification of the Epstein Barr Virus (EBV) BZLF1 Polypeptide in *E. coli*

The cDNA for the BZLF1 protein of the EBV strain B95-8 was amplified from the pCMVZ plasmid (Manet et al. (1990); EMBO 8:1819) by means of PCR using suitable PCR conditions (introductory denaturing step: 94° C., 2 min; followed by a three-stage PCR (15 cycles) with the following conditions: denaturing: 94° C., 30 sec; annealing 52° C., 1 min.; elongation: 72° C., 2 min; then again (25 cycles) with the following conditions: denaturing: 94° C., 30 sec; annealing 62° C., 1 min.; elongation: 72° C., 2 min; and a concluding polymerisation step at 72° C. for 10 min. followed by continuous cooling at 4° C.). In the PCR reaction to amplify the BZLF1 cDNA, 2.5% DMSO was added to the PCR formulation.

The primer A (5' primer: 5'-GGCGGAGATCTTTA-GAAATTTAAGAGATCC-3'; SEQ ID NO:1) and primer B (3' primer: 5'-GGCGGGGAATTCATGATGGAC-CCAAACTCG-3'; SEQ ID NO:2) were used for the amplification. The band amplified by means of the PCR was then cleaved with the restriction enzymes BglII and EcoRI and the band obtained in this fashion was then ligated into the plasmid-pET (New England Biolabs) also linearised with BglII and EcoRI. The vector thus produced was called pET5c-Z. The bacterial expression vector pET5c-Z was then transformed into the *E. coli* strain BL21-CodonPlus (DE3)-RIL (Carstens and Waesche (1999); Strategies; 12:49) and the transformed bacteria were cultured for 1 hour at 37° C. on LB Medium. Thereafter 50 µl of the culture was smeared on $LB_{AMP}$ plates and this was cultured overnight at 37° C. in an incubator. A single colony was then inoculated in 200 ml of LB Medium and this was incubated overnight at 37° C. Then, 10×1 liter of LB Medium was inoculated in each case with 1/50 volume of the total volume from the pre-culture and the cultures were then cultivated at 26° C. until an $O.D._{600}$ value of 0.8 was reached. The cultures were then mixed with 1 mM IPTG to stimulate the protein production and cultured further overnight.

To harvest the cells the culture was centrifuged for 10 min. at 5000 rpm in a GS 3 Rotor in a Sorvall cool centrifuge and the cell pellet obtained was resuspended in 250 ml of disintegration buffer (50 mM Tris Cl pH 8.0+0.3M NaCl+1 mM EDTA). The resuspended pellet was then frozen away at −20° C. for further processing. After thawing the cell pellet again, a spatula tip of lysozyme (muraminidase) was added to the cell suspension for the cell lysis and the formulation was incubated for 20 min at room temperature.

Then, 2 mM of the protease inhibitor Pefablock® was added to the formulation and this was then subjected to an ultrasound treatment on ice (3×1 min. at stage 6, pulsation: 80% using a Branson Sonifier, standard tip).

Then, 5 mM $MgCl_2$ and 2 U Benzonase®/ml protein extract was added to the formulation, the formulation was incubated for 20 min at 37° C. and then (sound suspension), centrifuged in a GSA-Rotor for 30 min. at 14000 rpm and 4° C. and the supernatant discarded. The pellet was then subjected to a fractionating washing with urea. In this case, after ultrasound disintegration the pellet was resuspended in 250 ml of 1M urea (in PBS without bivalent ions with 2 mM DTE) and the suspension was incubated for 1 hour in an overhead shaker at 4° C. The suspension was then centrifuged for 20 min. at 14000 rpm and the supernatant discarded. The pellet was then dissolved a second time, as described previously, by vortices in 1M urea, the suspension was centrifuged for 20 min. at 14000 rpm and the supernatant discarded. The pellet was then resuspended in 250 ml of 2 M urea (in PBS without bivalent ions with 2 mM DTE) and the suspension was incubated overnight in an overhead shaker at 4° C. The suspension was then centrifuged for 20 min. at 14000 rpm, the pellet was discarded and the supernatant was subjected to an acid precipitation. For this purpose the supernatant was titrated with 1N HCl to pH 3.5 and then centrifuged for 10 min at 12000 rpm. The pellet was discarded and the supernatant was dialysed 3× against a large volume (3.35 liter) of dialysis buffer (4M urea, 20 mM Tris Cl pH 7.5, 2 mM DTE). The suspension was then applied to a Poros QE anionic exchanger column and the column was washed with 15 column volumes of running buffer (4M urea, 20 mM Tris Cl pH 7.5). The protein was then eluted with 10 column volumes of 8M urea, 2M NaCl and various fractions were collected. The content and the purity of the BZLF1 protein in different fractions was determined by means of Coomassie and silver staining of the polypeptides separated by SDS-PAGE and by immuno blotting. Fractions which exhibit the BZLF1 protein with high purity were combined and mixed with 2 mM DTE. The BZLF1-containing suspension obtained was concentrated to about 5 ml using an Amikon stirring cell and a YM10 filter (disintegration volume 10 kDa) and the proteins in suspension were further separated by gel filtration chromatography. A Superdex 200 prep grade, Pharmacia-HiLoad, 16/60. 120 ml CV, flow rate: 0.5 ml/min was used for this purpose. The elution of the BZLF1 protein took place after about 0.4 column volumes. The clean BZLF1 fractions were combined and the protein content determined.

With this method the BZLF1 protein can be obtained with a yield of 3.9 mg/1 liter of culture and a purity of >95%.

After the purification the BZLF1 protein is present with a concentration of 0.2 to 1 mg/ml in 8 M urea, 2 mM DTE.

EXAMPLE 2

Detection of BZLF1-Specific Cytotoxic T Cells (CTL) from Peripheral Blood of an EBV Positive Donor Testing of the suitability of urea-denatured polypeptide and polypeptide present in urea solution for inducing an epitope presentation on MHC class I and II proteins as well as for simultaneously detecting polypeptide-specific CD4$^+$ and CD8$^+$ T cells in mixed APC/lymphocyte cultures was carried out using a very well characterised model system.

This is based on the observation that all HLA B8-positive, EBV-positive probands possess CD8$^+$ cytotoxic T cells which recognise a specific epitope (RAKFKQLL; amino acid 190-197; SEQ ID NO:3) within the EBV protein BZLF1 (Bogedain et al. (1995); J. Virol. 69:4872; Pepperl et al., (1998) J. Virol. 72:8644). In order to carry out the stimulation experiments, peripheral blood lymphocytes (PBMC) were obtained by means of density gradient centrifugation from heparinised whole blood (heparin final concentration: 25 IU/ml) of various EBV-negative, HLA B8-positive, or EBV-positive, HLA B8-negative or EBV-positive, HLA B8-positive probands. For this purpose 15 ml of Ficoll (PAN, Aidenbach) was placed in special 50 ml Leucosep tubes (Falcon, Becton Dickinson, Heidelberg) and coated with whole blood (diluted 2:1 with PBS). During the subsequent centrifugation (30 min, 800×g, swing-out rotor, room temperature), separation took place into plasma, lymphocyte population and erythrocytes. The desired lymphocyte population was removed and washed twice in approximately 30 ml of PBS. In each case, the cells were sedimented by brief centrifugation (5 min, 250×g, room temperature). The cell pellet was then taken up into T cell medium, the cell number was determined and the cells were either used in the corresponding experiments.

The depletion of CD8$^+$ cells from freshly prepared PBMC took place by negative selection using CD8 immunomagnetic MicroBeats following the manufacturer's protocol (Miltenyi Biotec, Bergisch Gladbach). Freshly isolated PBMC was washed, centrifuged (300×g, 10 min, 4° C.) and the cell pellet was resuspended in 80 µl PBS/10$^7$ PBMC. The desired cell population was magnetically marked by adding 20 µl of the specific Microbeads/10$^7$ PBMC during an incubation of 15 min at 4° C. The cell suspension was then washed twice (15 ml PBS), centrifuged and taken up in 500 µl PBS. For the magnetic separation MS$^+$ columns (for a maximum of 1×10$^7$ marked cells) or LS$^+$ columns (for a maximum of 1×10$^8$ marked cells) were used according to the cell number, equilibrated with 5 ml PBS, the cell suspension was applied and washed with 3×500 µl (MS$^+$ columns) or 3×5 ml (LS$^+$ columns) PBS. Non-marked cells pass through the column. The column was then removed from the magnetic field and the marked cell population was eluted by adding 500 µl (MS$^+$ columns) or 5 ml (LS$^+$ columns).

BZLF1-specific CD4$^+$ T helper cells and CD8$^+$ CTL were detected by means of an enzyme-linked immunospot assay (Elispot). Using Elispot, antigen-specific T cells can be detected using their cytokine secretion (especially the secretion of IFN-γ). Nitrocellulose-coated 96-well microtitre plates (MAHA S 45, Millipore, Eschborn) were coated with monoclonal, anti-human IFN-□ (Hölzl, Cologne) (5 µg/ml in PBS) and incubated overnight at 4° C. The antibody solution was pipetted off and the plates were washed four times with 200 µl PBS/formulation in each case.

In a following step non-specific binding sites were blocked by adding 200 µl of blocking buffer in each case (T cell medium with 10% FCS) during a one-hour incubation at 37° C. PBMC was used in a concentration of 2×10$^5$ cells/formulation in a volume of 100 µl of T cell medium/formulation (5 replicates each). Stimulation took place directly in the plate by adding 50 µl of antigen solution (final concentration: BZLF1: 5 µg/ml). After incubation for 24 hours (37° C., 5% CO$_2$) the cell suspension was drawn off and any cells still adhering were removed by washing five times (200 µl of PBS with 0.05% Tween 20 in each case, 5 min incubation with washing buffer in each case). The secondary, biotinylated antibody (1 µg/ml in PBS, 100 µl/formulation in each case) was then added; the plates were incubated for 2 hours at 37° C., then washed (5 times, 200 µl PBS/formulation in each case) and incubated for a further 2 hours using a streptavidin alkaline phosphatase (AP) conjugate (1 µg/ml in PBS; 200 µl/formulation in each case; Hölzl, Cologne). After a last washing step (5 times, 200 µl PBS/formulation in each case), the staining reaction took place by adding the enzyme substrate NBT/BCIP (Boehringer, Mannheim). A staining solution [200 µl NBT/BCIP stock solution to 10 ml of staining buffer (0.1 M tris-buffer, pH 9.5 with 0.05 M MgCl$_2$, 0.1 M NaCl)] was produced for this purpose and 200 µl/formulation was used in each case. After 5-10 min (donor-specific), the calorimetric reaction was stopped by washing the plates with deionised water. The plates were evaluated using an Elispot Reader (Biosys 2000, BioSys, Karben).

FIG. 1 shows the results of the IFN-□-elispot for the example of 8 donors (6 EBV-positive, 2 EBV-negative probands) after stimulation with urea-denatured BZLF1 polypeptide described above. PBMC of the EBV-negative (JW, BH) and/or B8-negative donors (LD, FN, JW, BH) were used as negative controls and showed no significant reactivity after antigen stimulation with urea-denatured BZLF1. In contrast, when using PBMC from the EBV-positive, HLA B8-positive donors (JU, SD, MB, RE) a significant to strong reactivity of BZLF1-specific, IFN-□ producing cells could be shown. As a result of the depletion of the CD8$^+$ T cells, the number of detectable IFN-□ producing ones was reduced significantly, which confirms the presence of BZLF1-specific cytotoxic T cells in the total population of peripheral blood lymphocytes.

EXAMPLE 3

Measurement of the virus-specific T-lymphocytes in heparinised whole blood 10 ml of whole blood was taken from a serologically positive donor in a Heparin Monovette (Sarstedt, Nümbrecht). From this respectively 2 ml was pipetted into a sterile Falcon Tube (No. 2059; B D Falcon, Heidelberg). One formulation represents the negative control, in this case only the pure monoclonal antibodies against the costimulatory molecules CD28 and CD49d (Becton Dickinson, Heidelberg) are to be added in a final concentration of 1 µg/ml. Another formulation is the positive control, in this case a superantigen is pipetted in addition to the monoclonal antibodies CD28 and CD49d. This is the *Staphylococcus* enterotoxin B (SEB), this is to be added in a final concentration of 1 µg/ml. In a third formulation the antigen used for the restimulation is to be added to the whole blood with the monoclonal antibodies. The concentration should be titrated out anew for each batch.

In our case, optimal results both with the synthetic peptide and with the modified protein could be achieved with a final concentration of 10 µg/ml. The tube was then incubated in a standard incubator (37° C., 5% $CO_2$ and $H_2O$-saturated atmosphere), standing with the lid loose (making gas exchange possible). After two hours Brefeldin A is added to the samples so that a final concentration of 10 µg/ml is achieved. The samples are thoroughly mixed on a Vortex and placed for another 4 hours in the incubator.

After a total of 6 hours short-term culture, 11% of the culture volume is pipetted into ice-cold EDTA solution (EDTA in PBS, 20 mM). The samples are briefly vortexed and then incubated for a maximum of 10 minutes at room temperature. The samples are then thoroughly vortexed again so that all the adherent cells are removed from the tube wall. Then at least 9 times the culture volume of FACS lysing solution (BD, Heidelberg) is to be added to the samples. The tubes are then incubated again for a maximum of 10 minutes at room temperature. The samples are then centrifuged at 4° C. for 8 minutes at 340 g. The supernatant is carefully decanted and the cells are then washed again with 5 ml FACS-buffer (PBS+0.1% w/v $NaN_3$+1% w/v FCS) and centrifuged again at 340 g for 8 minutes. The cells are then resuspended in a small quantity of FACS buffer and the cells are distributed on the tubes (e.g. Falcon No. 2054) for staining. At least $1\times10^6$ cells should be present per staining formulation. The permeabilising solution (PBS+0.1% w/v Saponin) is then pipetted to the cells in a quantity of 1 ml per $1\times10^6$ cells. The formulation is thoroughly vortexed and incubated for a maximum of 10 minutes at room temperature. The cells were then washed with 5 ml FACS buffer and centrifuged at 340 g for 8 minutes. The cells can then be stained. This takes place in a staining volume of 100 µl. The monoclonal antibodies are then added by pipetting in a ratio of FITC 1:10, PE 1:10, ECD 1:10 and APC 1:100. A typical 4-colour tube would then contain, for example, the antibodies CD3 FITC, anti-IFN-γ-PE, CD4 ECD and CD8 APC. The staining takes place for at least 30 minutes on ice (4° C.) and in the dark. The cells are then washed at least twice using 5 ml of FACS buffer and centrifuged for 8 minutes at 340 g after each washing step. For the measurement the cells are then taken up in at least 200 µl of FACS buffer. And immediately analysed using a flow cytometer. If the samples are not to be measured immediately, the cells can be fixed using 1% PFA (paraformaldehyde) in FACS buffer. Storage takes place at 4° C.

The results are then evaluated using one of the CellQuest Software (Becton Dickinson, Heidelberg). As an example the figures show the results for an EBV-seropositive patient showing the HLA-type B8. After permeabilising, the following stainings were carried out:

Formulation 1: control, unstained
Formulation 2: CD3 FITC/IFN-γ PE/CD4 ECD/CD8 APC
Formulation 3: CD3 FITC/IL-4 PE/CD4 ECD/CD8 APC
Formulation 4: CD3 FITC/CD8 PE/CD4 ECD/CD69 APC
Formulation 5: CD3 FITC/CD16 PE/CD8 ECD/CD56 APC
Formulation 6: CD3 FITC/perforin PE/CD8 ECD/CD4 APC
Formulation 7: CD3 FITC/isotype control PE/CD8 ECD/CD4 APC.

Figure 2B:
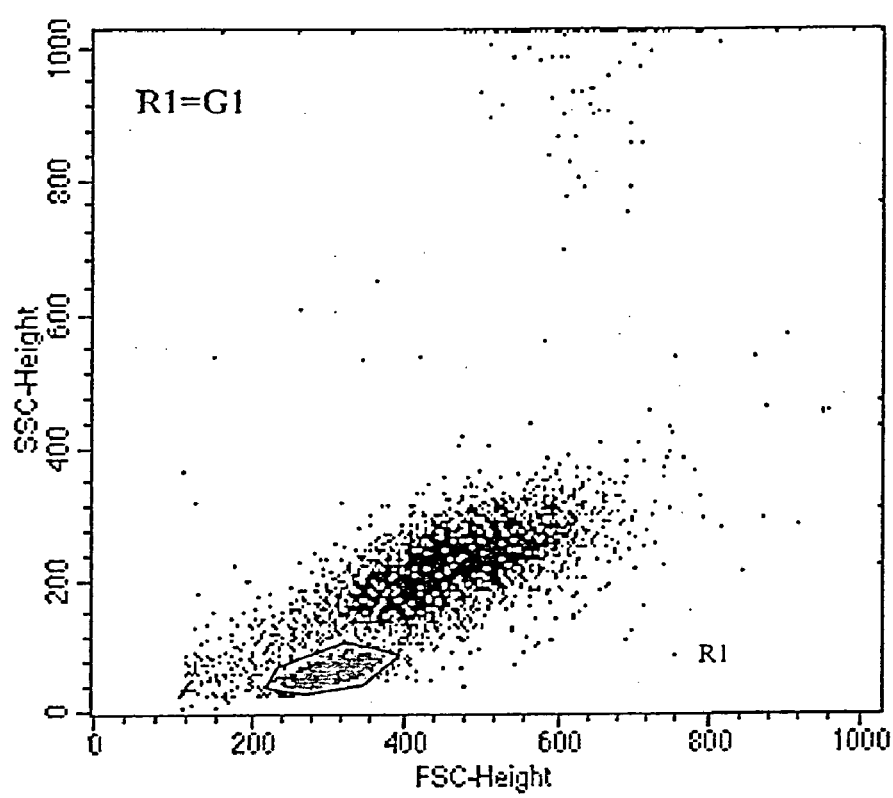

FIGS. 2a and b show the flow-cytometric analyses of whole blood after restimulation with synthetic peptide described above (FIG. 2a) or after restimulation with urea-denatured BZLF1 polypeptide (FIG. 2b). Shown is an FSC/SSC (Forward Scatter/Side Scatter) dotplot, wherein the measurement region given by R1 (Region 1) corresponds to the lymphocyte population. FIGS. 3a and b then show the frequency and distribution of various populations of CD3 and CD8-positive lymphocytes in whole blood after stimulating with urea-denatured BZLF1 polypeptide (FIG. 3a) or a synthetic BZLF1 peptide (FIG. 3a), which contains a known CTL epitope. In this case, it is clear that when stimulating with urea-adjuvated polypeptide, significantly more CD3 and CD8 weakly expressing cells can be retrieved.

FIGS. 4a and b show the frequency of the peripherally occurring double-positive ($CD4^+$ and $CD8^+$) lymphocyte populations in whole blood after stimulating with urea-adjuvated BZLF1 polypeptide (FIG. 4a) or a synthetic BZLF1 peptide (FIG. 4b) which contains a known CTL epitope. This figure also clearly shows the advantages of polypeptide restimulation which allows a considerably better analysis of the double-positive T-lymphocytes which can play an important role for the immune system in virus infections. Furthermore, the population of the weakly CD3 and CD8 expressing cells should be characterised more accurately with the staining of the surface markers CD16 and CD56. This is because both CD16 and also CD56 are markers which are typical of NK or NKT cells. Since the cells additionally express CD3, the NKT cells can thus be assigned. FIGS. 5a and b are dotplots showing the cell populations which exhibit expression of the surface markers CD8 and CD56. In both figures (FIGS. 5a and 5b), it can be clearly seen that the population of $CD3^+$ $CD8^+$ cells characterised by R3 in FIG. 2, here shown in blue, expresses CD56 on the cell surface. Thus, the cells shown in R3 express the population of the NKT cells.

Furthermore, with the detection of intracellular IFN-γ it should be shown that the T lymphocytes have been stimulated as part of a Th1 immune response and possess cytotoxic properties. In FIGS. 7a and b the histogram plots show the interferon-γ expression from various populations of all the lymphocytes registered in R1 after stimulation with urea-adjuvated BZLF1 polypeptide (FIG. 7a) or the BZLF1 peptide (FIG. 7b). Here M1 and M2 are set as markers. M1 designates the region in which the IFN-γ expression is to be classified as positive. Everything lying to the left thereof is to be explained by non-specific binding of the anti-IFN-γ antibody inside the cells. The region characterised by M2 shows the IFN-γ expression by the pure population of $CD3^+CD8^+$ cytotoxic T cells. The difference between the IFN-γ values shown in M1 and M2 characterises the IFN-γ production by weak CD8+ with NK cell properties.

After restimulating with urea-adjuvated BZLF1 polypeptide (FIG. 7a), a significantly increased IFN-γ production from cells of whole blood and an increased stimulation of the population of weakly CD8+ cells with NK cell properties can be observed compared to the peptide stimulation. The expression of intracellular IFN-γ content was then determined separately for the individual cell populations.

FIGS. 9a and b show histogram plots giving the IFN-7 expression of the population of CD8+ cytotoxic T cells from whole blood shown in R3 after stimulation with urea-adjuvated BZLF1 polypeptide (FIG. 9a) or the synthetic BZLF1 peptide (FIG. 9a). The markers M1 and M2 are set in accordance with FIGS. 7a and b. This figure shows that urea-adjuvated BZLF1 protein and the synthetic. BZLF1 peptide are equally suitable for determining BZLF1-specific cytotoxic T cells. However, the simultaneous readout of $CD8^{dim}$ cells was only possible after treating the cells with urea-adjuvated BZLF1 polypeptide.

This phenomenon then becomes clearer in FIGS. 11a and b. These show, in a histogram plot, the IFN-γ expression of NKT cell population designated by R4 after stimulating with urea-adjuvated BZLF1 polypeptide (FIG. 11a) or the synthetic BZLF1 peptide (FIG. 11b). This figure confirms the efficient stimulation of the weakly CD8-positive NKT cell population after stimulation with urea-adjuvated BZLF1 polypeptide.

To sum up, it can be shown using the examples that the conventional method corresponding to the prior art for reading out cytotoxic T lymphocytes by means of restimulation using synthetic peptides actually only allows an analysis of the CD8 highly positive T lymphocytes. When using urea-adjuvated polypeptides however, substantially more predictions can be made of other cell populations (such as for example $CD4^+CD8^{dim}$ lymphocytes or CD56+ NKT cells).

EXAMPLE 4

Induction of a Specific Antibody Response in Rabbits After Immunisation with Urea-Adjuvated BZLF1 Polypeptide In order to test the suitability of urea-adjuvated BZLF-1 polypeptide, 30 μg of BZLF1 polypeptide in 8M urea was adjuvated with Hunters Titermax as specified by the manufacturer (Sigma) and administered intramuscularly to a rabbit. The animal was re-immunised with the same immunogen 4 and 8 week as after the basic immunisation. After a further 3 weeks, blood was taken from the animal and the serum obtained therefrom was tested in different dilutions (1:2000; 1:10000 and 1:50000) in the immunoblot for the presence of BZLF1 specific antibodies. For this purpose BZLF1 polypeptide produced recombinantly in E. coli in various concentrations (20 ng, 100 ng and 500 ng) was separated in a 12.5% SDS gel and the proteins were then transferred onto nitrocellulose. After the protein transfer the still-free protein binding sites on the nitrocellulose were saturated by incubating with a 5% solution of skimmed milk powder in TBS (500 mM NaCl, 25 mM Tris pH 7.5), shaking slightly. The Blot was then washed four times with TTBS for at least 10 min before it was incubated for 1 to 12 hours with the corresponding dilution of the rabbit serum in TBS.

Detection via an enzyme/substrate-mediated colour reaction: After the binding of the specific antibody, the nitrocellulose filter was again washed four times with TTBS for 10 min and then shaken for at least 1 hour with a suitable dilution of an anti-immunoglobulin coupled with alkali phosphatase (AP) or horseradish peroxidase (HRP).

After a further washing step (four times for 10 min using TTBS), the filter was incubated with the chromogenic substrates of the alkali phosphatase (68 μl NBT, 70 μl BCIP in 20 ml AP-buffer: 100 mM NaCl, 50 mM $MgCl_2$, 100 mM Tris (Sambrook et al. 1989)) or horseradish peroxidase (2.5 ml Tris/HCl pH 7.5, 1 spatula tip of 3,3'-diaminobenzidine, 30 μl 30% $H_2O_2$, to 50 ml with $H_2O_{bid.}$). The resulting enzyme reactions produced a brown colour after minutes to hours. The reactions were stopped with $H_2O_{bid.}$.

These studies showed that polypeptide dissolved in 8M urea is suitable for inducing high-titre polypeptide-specific antibodies. It was shown that the serum of the experimental animal after three immunisations still contains sufficient BZLF1 antibody in a dilution of 1:50000 to detect 100 ng of purified BZLF1 polypeptide in the immunoblot (FIG. 12). The urea contained in the injection solution additionally proved to be non-toxic for the experimental animal.

EXAMPLE 5

Influence of Urea on the Vitality of Purified Population of Peripheral Blood Mononuclear Cells (PBMC)

In order to test the influence of urea on the cell vitality, PBMC, as described in Example 2, were purified from the heparinised whole blood of 3 healthy donors (DH, SB, IK) and respectively $1 \times 10^6$ cells in four replicates in T-cell medium (RPMI 1640 with 5% human serum, 2 mM glutamine and 100 U/ml penicillin/100 μg/ml streptomycin (all components from PanSystems, Aidenbach)) was mixed with increasing concentrations of urea (0, 0.05, 0.1, 0.2, 0.3, 0.4, 0.8 or 1.6 mol/liter) and incubated in wells of a 48-well microtitre plate for 17 hours in an incubator with humidified atmosphere and 5% $CO_2$ gassing at 37° C. An 8M urea stock solution which was mixed with 2M NaCl and 2 mM DTE was used for these experiments. The cells were then resuspended in the cultivation formulation by repeatedly pipetting the medium on and off and the total number of cells and the ratio of the living to dead cells was determined using a Neubauer "improved" counting chamber after staining with a Trypan blue solution (0.5% w/v). The results of these investigations are given in Table 1. These investigations showed that compared to the untreated cells, the addition of urea in a concentration range of 0 to 0.2 mol/liter results in no significant reduction in the ratio of living to dead cells in the mixture of peripheral mononuclear cells. When 0.3 mol/liter of urea was added, a significantly increased number of dead cells was to be observed; from a urea concentration of 0.4 mol/liter, more dead than living cells were present in the PBMC cultures after incubation for 17 hours, regardless of the donor. The addition of urea in concentrations above 0.3 mol/liter also resulted in a significant reduction in the total number of cells, which indicates that urea has a cytolytic effect at these concentrations.

TABLE 1

Influence of the urea concentration on the vitality of PBMCs

| C[urea] | D.H. Cell number | D.H. Living/dead | S.B. Cell number | S.B. Living/dead | I.K. Cell number | I.K. Living/dead |
|---|---|---|---|---|---|---|
| 0 mol/liter | $1.44 \times 10^6$ | 0.5 | $1.33 \times 10^6$ | 34.4 | $1.5 \times 10^6$ | 121 |
| 0.05 mol/liter | $0.62 \times 10^6$ | 15.9 | $1.03 \times 10^6$ | 2.2 | $1.1 \times 10^6$ | 11.7 |
| 0.1 mol/liter | $0.56 \times 10^6$ | 1.7 | $1.41 \times 10^6$ | 55 | $1.6 \times 10^6$ | 41.3 |
| 0.2 mol/liter | $0.47 \times 10^6$ | 6.6 | $1.94 \times 10^6$ | 3.6 | $5.1 \times 10^6$ | 30.2 |
| 0.3 mol/liter | n.d. | n.d. | $0.36 \times 10^6$ | 1.8 | $0.7 \times 10^6$ | 9 |
| 0.4 mol/liter | $0.02 \times 10^6$ | 1 | $0.48 \times 10^6$ | 0.2 | $0.3 \times 10^6$ | 0.2 |
| 0.8 mol/liter | $0.05 \times 10^6$ | 0.1 | $0.35 \times 10^6$ | 0.04 | $2.9 \times 10^6$ | 0.02 |
| 1.6 mol/liter | $0.91 \times 10^6$ | 0.06 | $0.76 \times 10^6$ | 0 | $0.4 \times 10^6$ | 0 | n.d.: not determined; living/dead cell ratio = 0: that is, exclusively dead cells in the formulation, for less than 1 there are more dead than living cells in the formulation.

EXAMPLE 6

Influence of Urea on the Cytokine Secretion from Purified Population of Peripheral Blood Mononuclear Cells (PBMC)

Furthermore, it should be clarified by ELIspot analyses whether urea in populations of purified PBMCs triggers the secretion of cytokines, especially IFN-γ. For this purpose, 96-well nitrocellulose-coated microtitre plates, as described in detail in Example 2, were coated with a monoclonal anti-human IFN-γ antibody (Hölzl, Cologne) (5 µg/ml in PBS) and incubated overnight at 4° C. The antibody solution was pipetted off and the plates were washed four times using 200 µl PBS/formulation in each case. In a following step non-specific binding sites were blocked by adding 200 µl of blocking medium in each case (RPMI with 10% FCS) during a one-hour incubation at 37° C.

PBMC of a healthy donor (SB) were taken up in a concentration of respectively $2 \times 10^5$ purified PBMC/150 µL in T-cell medium containing different urea concentrations (0, 0.05, 0.1, 0.2, 0.3, 0.4, 0.8, and 1.6 mol/liter) (5 replicates each) and the stimulation formulations were incubated for 24 hours in an incubator with a humidified atmosphere with 5% $CO_2$ gassing at 37° C. An 8M urea stock solution which was mixed with 2M NaCl and 2 mM DTE was used for these experiments. The cell suspension was then drawn off and any cells still adhering were removed by washing six times (in each case 200 µl PBS with 0.1% Tween 20, 3 min incubation with washing buffer in each case). The secondary biotinylated antibody (1 µg/ml in PBS, 100 µl/formulation in each case) was then added; the plates were incubated for 2 hours at RT, then washed (6 times, 200 µl PBS/formulation in each case) and incubated for 1 hour with a streptavidin alkaline phosphatase (AP) conjugate (1 µg/ml in PBS; 100 µl/formulation in each case; Hölzl, Cologne). After a last washing step (6 times 200 µl PBS/formulation in each case), the colour reaction took place by adding the enzyme substrate NBT/BCIP (Boehringer, Mannheim). For this purpose a staining solution was prepared [200 µl NBT/BCIP-stock solution to 10 ml staining buffer (0.1 M tris-buffer, pH 9.5 with 0.05 M $MgCl_2$, 0.1 M NaCl)] and 100 µl/formulation was used in each case.

After 10 min the calorimetric reaction was stopped by washing the plates with deionised water (Biosys 2000, BioSys, Karben).

Table 2 shows the results of the IFN-γ-Elispot for the example of a donor after stimulation using the urea concentrations described previously. These investigations showed that after adding different concentrations of urea, no significantly increased release of IFN-γ is induced from cultures of peripheral blood mononuclear cells.

TABLE 2

Influence of urea concentration on IFN-γ secretion from PBMCs
S.B.

| c[urea] | Spots/$2 \times 10^6$ cells | Standard deviation |
|---|---|---|
| 0 mol/liter | 18.4 | 5.46 |
| 0.05 mol/liter | 26.2 | 12.9 |
| 0.1 mol/liter | 29.6 | 9.99 |
| 0.2 mol/liter | 26.4 | 16.5 |
| 0.3 mol/liter | 11.0 | 4.15 |
| 0.4 mol/liter | 18.2 | 3.12 |
| 0.8 mol/liter | 14.6 | 3.56 |
| 1.6 mol/liter | 13.4 | 1.74 |

EXAMPLE 7

Dose Dependence of IFN-γ Secretion After Stimulation with Urea-Treated BZLF-1 Protein The suitability of denatured polypeptides and polypeptides present in urea solution for inducing an epitope presentation on MHC class I and II proteins as well as for simultaneously detecting polypeptide-specific CD4+ and CD8+ T cells in mixed APC/lymphocyte cultures was tested using a very thoroughly characterised model system. This is based on the observation that all HLA B8-positive, EBV-positive probands possess CD8+ cytotoxic T cells which recognize a specific epitope (RAKFKQLL; amino acid 190-197; SEQ ID NO:3) inside the EBV protein BZLF1 (Bogedain et al. (1995); J. Virol. 69:4872; Pepperl et al., (1998) J. Virol. 72:8644). In order to test the optimal protein concentration to detect BZLF-1 specific T cell responses, purified peripheral blood lymphocytes (PBMC) from various EBV-negative, HLA B8-positive (donor 1), or EBV-positive, HLA B8-negative (donors 2,3) or EBV-positive, HLA B8-positive probands (donors 4-7) were incubated with various concentrations of urea-adjuvated BZLF-1 proteins and the IFN-γ secretion after 17 hours was determined using the ELIspot method.

For this purpose, nitrocellulose-coated 96-well microtitre plates, as described in detail in Example 2, were coated with a monoclonal, anti-human IFN-γ antibody (Hölzl, Cologne) (5 µg/ml in PBS) and incubated overnight at 4° C.

The antibody solution was pipetted off and the plates were washed four times using 200 µl PBS/formulation in each case. In a following step non-specific binding sites were blocked by adding 200 µl of blocking medium (RPMI with 10% FCS) in each case during a one-hour incubation at 37° C.

PBMCs from the seven probands in a concentration of $2 \times 10^5$ purified PBMC/150 μL in each case, were then taken up in T cell medium containing different concentrations of urea-adjuvated BZLF-1 protein (0.5 μg/ml, 2 μg/ml, 5 μg/ml, 20 μg/ml) (5 replicates each) and the stimulation formulations were incubated for 24 hours in an incubator with humidified atmosphere with 5% $CO_2$ gassing at 37° C. BZLF-1 protein which was present with a concentration of 1 mg/ml in an 8 molar urea with 2M NaCl and 2 mM DTE was used for these experiments. The cell suspension was then drawn off and any cells still adhering were removed by washing 6 times (200 μl PBS with 0.1% Tween 20 in each case, 3 min incubation with washing buffer in each case). The secondary biotinylated antibody was then added (1 μg/ml in PBS, 100 μl/formulation in each case) was then added; the plates were incubated for 2 hours at RT, then washed (6 times 200 μl PBS/formulation in each case) and incubated for 1 hour using a streptavidin alkaline phosphatase (AP) conjugate (1 μg/ml in PBS; 100 μl/formulation in each case; Hölzl, Cologne). After a last washing step (6 times 200 μl PBS/formulation in each case), the colour reaction took place by adding the enzyme substrate NBT/BCIP (Boehringer, Mannheim). For this purpose a staining solution was prepared [200 μl NBT/BCIP-stock solution to 10 ml staining buffer (0.1 M tris-buffer, pH 9.5 with 0.05 M $MgCl_2$, 0.1 M NaCl)] and 100 μl/formulation was used in each case.

After 5-10 min (donor-specific) the calorimetric reaction was stopped by washing the plates with deionised water. The plates were evaluated on an Elispot reader (Biosys 2000, BioSys, Karben).

TABLE 3

Relationship of the BZLF1 protein concentration to the urea concentration

| c[BZLF1] | c[urea] |
|---|---|
| 5 μg/ml | 0.04 mol/liter |
| 10 μg/ml | 0.08 mol/liter |
| 20 μg/ml | 0.16 mol/liter |
| 30 μg/ml | 0.24 mol/liter |

Relationship of the BZLF1 protein concentration to the urea concentration using a stock solution containing 1 μg/μl BZLF1 protein in 8 mol/liter urea, 2 mol/liter NaCl, 2 mmol/liter 1,4-dithioerythritol (DTE).

The results of this experiment are shown in FIG. 13. The investigations showed that the BPMCs of 2 out of the 4 tested HLA-B8-positive, EBV-positive donors at all the BZLF-1 concentrations tested showed a significantly increased number of IFN-γ producing BZLF-1-specific T cells compared to the negative controls (donors 1-3). In these experiments low concentrations of the urea-adjuvated BZLF-1 protein were already sufficient to detect a significantly increased number of BZLF-1-specific IFN-γ producing T cells compared to the negative controls (donors 1-3) in 3 out of 4 HLA-B8-positive, EBV-positive donors. The optimal stimulation of interferon-γ production was to be observed after stimulation with 5 or 20 μg/ml urea-adjuvated BZLF-1 protein specific to the donor. After stimulating PBMCs of control probands 1 and 3 with urea-adjuvated BZLF-1 protein in concentrations of 2 to 20 μg/ml, a small number of IFN-γ secreting PBMCs could be detected. These reactivities are possibly based on the stimulation of CD8+ T cell which are directed against hitherto unknown target epitopes within the BZLF-1 protein. Furthermore, the observed spot may come from BZLF-1-specific CD4+ cells which are excited to IFN-γ production by the stimulation with urea-adjuvated BZLF-1 protein.

EXAMPLE 8

Time Behaviour of IFN-γ Secretion After Stimulation with Urea-Treated BZLF-1 Protein In order to test the optimal stimulation time to detect BZLF-1-specific T cell responses, purified peripheral blood lymphocytes (PBMC) from various EBV-negative, HLA B8-positive (donor 1), or EBV-positive, HLA B8-negative (donors 2,3) or EBV-positive, HLA B8-positive probands (donors 4-7) were incubated for varying times using 10 μg/ml urea-adjuvated BZLF-1 proteins in each case and the IFN-γ secretion was determined using the ELIspot method.

For this purpose nitrocellulose-coated 96-well microtitre plates, as already described in detail, were coated with a monoclonal, anti-human IFN-γ antibody and non-specific binding sites were blocked by adding blocking medium (RPMI with 10% FCS). Then PBMCs of the seven probands in a concentration of $2 \times 10^5$ purified PBMC/150 μL in each case were taken up in T-cell medium using 10 μg/ml urea-adjuvated BZLF-1 protein (5 replicates in each case) and the stimulation formulations were incubated for 2, 8, 16 or 24 hours in an incubator with humidified atmosphere with 5% $CO_2$ gassing at 37° C. BZLF-1 protein which was present in a concentration of 1 mg/ml in an 8 molar urea with 2M NaCl and 2 mM DTE was used for these experiments. The IFN-γ ELIspot Assay was carried out as described in detail in the preceding example.

The results of this experiment are shown in FIG. 14. The investigations showed that after incubation for 8 hours all HLA-B8-positive, EBV-positive donors (donors 4-7) show a significantly increased number of IFN-γ producing BZLF-1-specific T cells compared with all "control probands" (donors 1-3). The maximum number of IFN-γ producing cells could be observed after 16 to 24 hours depending on the donor.

The invention claimed is:

1. A method for the detection of polypeptide-specific $CD4^-$ $CD8^+$ T cells comprising the following steps:
 a) incubating polypeptides with a urea solution;
 b) mixing APC-containing cell cultures or APC-containing body fluids in solution with the polypeptides of step a), wherein the mixture has a final urea concentration in the range of 0.001 to 0.2 mol/liter;
 c) incubating the APC-containing cell cultures or body fluids obtained according to step b) with T cells or T-cell-containing body fluids;
 d) detecting and/or quantifying T cells which are specific against the polypeptides from step a), wherein the detected and/or quantified T cells are $CD4^-CD8^+$ T cells.

2. The method according to claim 1, wherein the APC-containing cell culture is a PBMC population, isolated monocytic cells or a separated APC population, and wherein the APC-containing body fluid is whole blood.

3. The method according to claim 2, wherein the PBMC population is a leukapheresate.

4. The method according to claim 2, wherein the separated APC population has dendritic cells, monocytes, macrophages or B cells.

5. The method according to claim 4, wherein the dendritic cells are Langerhans cells.

6. The method according to claim 1, wherein the T-cell-containing body fluids are whole blood.

7. The method according to claim 1, wherein the detection and/or the quantification is carried out by detection of specific surface markers for T cells and IFNγ, IL4 or IL5.

8. The method according to claim 1, wherein the detection is carried out using FACS, ELISA or Elispot methods.

9. The method according to claim 1, wherein the polypeptides in step a) have a concentration in the range of about 0.01 μg/μl to about 50 μg/μl.

10. The method according to claim 1, wherein the polypeptides in step b) have a concentration in the range of about 0.1 μg to about 200 μg for approximately $10^6$ cells.

* * * * *

UNITED STATES PATENT AND TRADEMARK OFFICE
CERTIFICATE OF CORRECTION

| | | |
|---|---|---|
| PATENT NO. | : 7,829,331 B2 | Page 1 of 1 |
| APPLICATION NO. | : 10/508642 | |
| DATED | : November 9, 2010 | |
| INVENTOR(S) | : Hans Wolf et al. | |

It is certified that error appears in the above-identified patent and that said Letters Patent is hereby corrected as shown below:

On title page, item (54), line 3, and in the specification, column 1, line 3, delete "TREATMENT" and insert --THERAPY-- therefor.

Signed and Sealed this
Eighth Day of February, 2011

David J. Kappos
*Director of the United States Patent and Trademark Office*